(12) United States Patent
Wilbanks et al.

(10) Patent No.: US 12,037,590 B2
(45) Date of Patent: Jul. 16, 2024

(54) SHORT DNA APTAMERS AND METHODS FOR PROMOTING REMYELINATION

(71) Applicant: Mayo Foundation for Medical Education and Research, Rochester, MN (US)

(72) Inventors: Brandon A. Wilbanks, Rochester, MN (US); John A. Smestad, Rochester, MN (US); Moses Rodriguez, Rochester, MN (US); Louis J. Maher, III, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 614 days.

(21) Appl. No.: 17/298,803

(22) PCT Filed: Dec. 6, 2019

(86) PCT No.: PCT/US2019/065010
§ 371 (c)(1),
(2) Date: Jun. 1, 2021

(87) PCT Pub. No.: WO2020/118218
PCT Pub. Date: Jun. 11, 2020

(65) Prior Publication Data
US 2022/0033821 A1    Feb. 3, 2022

Related U.S. Application Data

(60) Provisional application No. 62/776,207, filed on Dec. 6, 2018.

(51) Int. Cl.
| C12N 15/115 | (2010.01) |
| A61K 31/7088 | (2006.01) |
| C12Q 1/68 | (2018.01) |

(52) U.S. Cl.
CPC ........ *C12N 15/115* (2013.01); *A61K 31/7088* (2013.01); *C12N 2310/16* (2013.01)

(58) Field of Classification Search
None
See application file for complete search history.

(56) References Cited

U.S. PATENT DOCUMENTS

| 9,150,867 | B2 | 10/2015 | Maher, III et al. |
| 9,481,887 | B2 | 11/2016 | Maher, III et al. |
| 9,809,823 | B2 | 11/2017 | Maher, III et al. |
| 2006/0193821 | A1 | 8/2006 | Diener et al. |
| 2007/0105805 | A1 | 5/2007 | Kmiec et al. |
| 2008/0233132 | A1 | 9/2008 | Miller et al. |
| 2009/0234105 | A1 | 9/2009 | Gervay-Hague et al. |
| 2010/0074907 | A1 | 3/2010 | Mi et al. |
| 2012/0165401 | A1 | 6/2012 | Nakamura et al. |
| 2014/0148501 | A1 | 5/2014 | Maher, III et al. |
| 2016/0017333 | A1 | 1/2016 | Maher, III et al. |
| 2017/0088839 | A1 | 3/2017 | Maher, III et al. |

FOREIGN PATENT DOCUMENTS

| EP | 1964574 | 9/2008 |
| WO | WO 1995/030004 | 11/1995 |
| WO | WO 2001/085797 | 11/2001 |
| WO | WO 2004/110355 | 12/2004 |
| WO | WO 2010/008588 | 1/2010 |

OTHER PUBLICATIONS

Alleti et al., "A Solanesol-Derived Scaffold for Multimerization of Bioactive Peptides," J. Org. Chemistry, 75(17):5895-5903, Aug. 11, 2010.
Andreola et al., "DNA Aptamers Selected against the HIV-1 RNase H Display in Vitro Antiviral Activity," Biochemistry, 40(34):10087-10094, Aug. 3, 2001.
Bailey et al., "Fitting a mixture model by expectation maximization to discover motifs in biopolymers," Proceedings of the Second International Conference on Intelligent Systems for Molecular Biology, 2:28-36, Aug. 1994.
Banga, "Theme Section: Transdermal Delivery of Proteins," Pharm. Research, 24(7):1357-1359, Jul. 2007.
Bates, "Treatment effects of immunomodulatory therapies at different stages of multiple sclerosis in short-term trials," Neurology, 76(1 Suppl 1):S14-25, Jan. 4, 2011.
Bieber et al., "Human Antibodies Accelerate the Rate of Remyelination Following Lysolecithin-Induced Demyelination in Mice," Glia, 37(3):241-249, Mar. 1, 2002.
Bryan et al., "G-Quadruplexes: From Guanine Gels to Chemotherapeutics," Mol. Biotechnology, 49(2):198-208, Mar. 17, 2011.
Campagnoni, "Molecular biology of myelin proteins from the central nervous system.," J. Neurochemistry, 51(1):1-14, 1988.
Chang et al., "Facile Supermolecular Aptamer Inhibitors of L-Selectin," PLoS One, 10(3):e0123034, Mar. 31, 2015, 16 pages.
Compston et al., "Multiple sclerosis," Lancet, 359(9313):1221-1231, Apr. 6, 2002.
Dougan et al., "Extending the Lifetime of Anticoagulant Oligodeoxynucleotide Aptamers in Blood," Nuclear Med. Biology, 27(3):289-297, Apr. 2000.
Freedman, "Long-term follow-up of clinical trials of multiple sclerosis therapies," Neurology, 76(1 Suppl 1):S26-34, Jan. 4, 2011.
GenBank Accession No. FS078931.1, "FS078931 library SmFL Solanum melongena cDNA clone SmFL18L20 5', mRNA sequence," dated Dec. 29, 2009, 1 page.
Goebel et al., "Dermal Peptide Delivery Using Colloidal Carrier Systems," Skin Pharmacol. Physiology, 21(1):3-9, 2008.
Govan et al., "Stabilization and Photochemical Regulation of Antisense Agents through PEGylation," Bioconjugate Chemistry, 22(10):2136-2142, Sep. 20, 2011.
Griffin et al., "The discovery and characterization of a novel nucleotide-based thrombin inhibitor," Gene, 137(1):25-31, Dec. 27, 1993.
Heider et al., "An Assay that Predicts In Vivo Efficacy for DNA Aptamers that Stimulate Remyelination in a Mouse Model of Multiple Sclerosis," Mol. Ther. Methods Clin. Development, 9:270-277, Mar. 21, 2018.

(Continued)

*Primary Examiner* — Sean McGarry
(74) *Attorney, Agent, or Firm* — Fish & Richardson P.C.

(57) ABSTRACT

Materials and methods related to using short DNA aptamers to treat demyelinating diseases are provided herein.

16 Claims, 28 Drawing Sheets

Specification includes a Sequence Listing.

(56) References Cited

OTHER PUBLICATIONS

Huisgen, "1,3-Dipolar Cycloadditions. Past and Future," Angew Chem. Int. Edition, 2(10):565-598, Oct. 1963.
Ishiguro et al., "Therapeutic Potential of Anti-Interleukin-17A Aptamer: Suppression of Interleukin-17A Signaling and Attenuation of Autoimmunity in Two Mouse Models," Arthritis Rheumatism, 63(2):455-466, Feb. 2011.
Maier et al., "A New Transferrin Receptor Aptamer Inhibits New World Hemorrhagic Fever Mammarenavirus Entry," Mol. Ther. Nucleic Acids, 5:e321, Jan. 2016, 15 pages.
Malik et al., "Recent Advances in Protein and Peptide Drug Delivery Systems," Curr. Drug Delivery, 4(2):141-151, Apr. 2007.
Mayr et al., "Incidence and prevalence of multiple sclerosis in Olmsted County, Minnesota, 1985-2000," Neurology, 61(10):1373-1377, Nov. 25, 2003.
McGavern et al., "Quantitation of Spinal Cord Demyelination, Remyelination, Atrophy, and Axonal Loss in a Model of Progressive Neurologic Injury," J. Neurosci. Research, 58(4):492-504, Nov. 15, 1999.
Mitsunaga et al., "Direct evidence that a human antibody derived from patient serum can promote myelin repair in a mouse model of chronic-progressive demyelinating disease," FASEB Journal, 16(10):1325-1327, Aug. 2002.
Nastasijevic et al., "Remyelination induced by a DNA aptamer in a mouse model of multiple sclerosis," PLoS One, 7(6):e39595, Jun. 27, 2012, 8 pages.
Nastasijevic et al., "Sequence-specific binding of DNA and RNA to immobilized Nickel ions," Biochem. Biophys. Res. Communications, 366(2):420-425, Feb. 8, 2008.
Noseworthy et al., "Multiple sclerosis," New Engl. J. Med., 343(13):938-952, Sep. 28, 2000.
Paz Soldán et al., "Remyelination-promoting antibodies activate distinct Ca2+ influx pathways in astrocytes and oligodendrocytes: relationship to the mechanism of myelin repair," Mol. Cell. Neuroscience, 22(1):14-24, Jan. 2003.
PCT International Preliminary Report on Patentability in International Appln. No. PCT/US2019/065010, dated Jun. 8, 2021, 7 pages.
PCT International Search Report and Written Opinion in International Appln. No. PCT/US2019/065010, dated Apr. 28, 2020, 11 pages.
Perschbacher et al., "Quantitative PCR Analysis of DNA Aptamer Pharmacokinetics in Mice," Nucleic Acid Therapeutics, 25(1):11-19, Jan. 19, 2015.
Perwein et al., "A comparison of human natural monoclonal antibodies and aptamer conjugates for promotion of CNS remyelination: where are we now and what comes next?," Expert Opin. Biol. Therapy, 18(5):545-560, Feb. 25, 2018.
Prausnitz, "A peptide chaperone for transdermal drug delivery," Nat. Biotechnology, 24(4):416-417, Apr. 2006.
Rodriguez et al., "Immune Response Gene products (Ia antigens) on glial and endothelial cells in virus-induced demyelination," J. Immunology, 138(10):3438-3442, May 15, 1987.
Rodriguez et al., "Immunoglobulins reactive with myelin basic protein promote CNS remyelination," Neurology, 46(2):538-545, Feb. 1996.
Rodriguez, "Impairment, disability, and handicap in multiple sclerosis: a population-based study in Olmsted County, Minnesota," Neurology, 44(1):28-33, Jan. 1994.
Rostovtsev et al., "A Stepwise Huisgen Cycloaddition Process: Copper(I)-Catalyzed Regioselective "Ligation" of Azides and Terminal Alkynes," Angew Chem. Int. Edition, 41(14):2596-2599, Jul. 15, 2002.
Shchepinov, "Oligonucleotide Dendrimers: from Polylabelled DNA Probes to Stable Nano-Structures," Glen Report, 12(1):1-4, Nov. 1999.
Smestad et al., "Ion-dependent conformational switching by a DNA aptamer that induces remyelination in a mouse model of multiple sclerosis," Nucleic Acids Research, 41(2):1329-1342, Jan. 2013.
Soldan et al., "Remyelination-promoting antibodies activate distinct Ca2+ influx pathways in astrocytes and oligodendrocytes: relationship to the mechanism of myelin repair," Mol. Cell. Neuroscience, 22(1):14-24, Jan. 2003.
Somasunderam et al., "Combinatorial selection, inhibition, and antiviral activity of DNA thioaptamers targeting the RNase H domain of HIV-1 reverse transcriptase," Biochemistry, 44(30):10388-10395, Aug. 2, 2005.
Stephanopoulos et al., "Dual-Surface Modified Virus Capsids for Targeted Delivery of Photodynamic Agents to Cancer Cells," ACS Nano, 4(10):6014-6020, Oct. 26, 2010.
The Glen Report, "An Unnatural Base Pair System for the Expansion of Genetic Information," Glen Research, 20(1):1, May 8-9, 2008.
Tucker et al., "Detection and plasma pharmacokinetics of an antivascular endothelial growth factor oligonucleotide-aptamer (NX1838) in rhesus monkeys," J. Chromatogr. B Biomed. Sci. Applications, 732(1):203-212, Sep. 10, 1999.
Villar-Guerra et al., "G-Quadruplex Secondary Structure Obtained from Circular Dichroism Spectroscopy," Angew. Chem. Int. Edition, 57(24):7171-7175, Oct. 26, 2017.
Wang et al., "Aptamer Antagonists of Myelin-Derived Inhibitors Promote Axon Growth," PLoS One, 5(3):e9726, Mar. 16, 2010, 8 pages.
Wang et al., "Inhibition of midkine alleviates experimental autoimmune encephalomyelitis through the expansion of regulatory T cell population," Proc. Natl. Acad. Sci. USA, 105(10):3915-3920, Mar. 4, 2008.
Warrington et al., "Human monoclonal antibodies reactive to oligodendrocytes promote remyelination in a model of multiple sclerosis," Proc. Natl. Acad. Sci. USA, 97(12):6820-6825, Jun. 6, 2000.
Wermeling et al., "Microneedles permit transdermal delivery of a skin-impermeant medication to humans," Proc. Natl. Acad. Sci. USA, 105(6):2058-2063, Feb. 12, 2008.
Williamson et al., "Monovalent cation-induced structure of telomeric DNA: The G-quartet model," Cell, 59(5):871-880, Dec. 1989.
Williamson, "G-quartet structures in telomeric DNA," Annu. Rev. Biophys. Biomol. Structure, 23:703-730, Jun. 1994.
Wright et al., "Aptamers selected from myelin substrates used as alternatives to antibodies to study, diagnose and treat demyelinating diseases," J. Neurochemistry, 104(Suppl. 1):120, Abstract PTW05-16, 2008, 2 pages.
Wright et al., "Aptamers selected from myelin substrates used as alternatives to antibodies to study, diagnose and treat demyelinating diseases," Poster, Presented at the 29th Annual Meeting of the American Society for Neurochemistry, Mar. 1-5, 2008, 1 page.
Yim et al., "Synthesis of DOTA-conjugated multimeric [Tyr3]octreotide peptides via a combination of Cu(I)-catalyzed "click" cycloaddition and thio acid/sulfonyl azide "sulfo-click" amidation and their in vivo evaluation," J. Med. Chemistry, 53(10):3944-3953, Apr. 22, 2010.

FIG. 3A

Aptamer 3064 (G-rich 40-mer)

5'-Fluor-*GGGTCGGCGGGTGGGGTGGGAGGTGGTCTTGTCTCTGGGT*-3'-Biotin (SEQ ID NO:1)

Negative control aptamer 3060

5'-Fluor-AAAGAACAAAAAGGATAAAGGGGGAGACGGGGGAACATGGGG-3'-Biotin (SEQ ID NO:2)

Negative control aptamer 5707

5'-Fluor-T40-3'-Biotin (SEQ ID NO:3)

Negative control aptamer 5733

5'-Fluor-T20-3'-Biotin (SEQ ID NO:4)

20-mer "core" of 3064

5'-Fluor-GGGTCGGCGGGTGGGGTGGG-3'-Biotin (SEQ ID NO:5)

SELEX-optimized 20-mer derivative of 3064 (Aptamer 5708)

5'-Fluor-GGGTTAGCGGGTGAGGTGGG-Spacer18-3'-Biotin (SEQ ID NO:6)

FIG. 3B

Recovered Sequence Pool

| Sequence | Identifier |
|---|---|
| GGGTCGGCGGGTGGGTGGG | 20-mer "core" (SEQ ID NO:5) |
| GGGTTAGCGGGTGAGGTGGT | 5706 (SEQ ID NO:7) |
| GGGTTAGCGGGTGAGGTGGT | 5706 (SEQ ID NO:7) |
| GGGTTAGCGGGTGAGGTGGT | 5706 (SEQ ID NO:7) |
| GNGTTAGCGGGTGGGGTGAG | (SEQ ID NO:8) |
| GGGTTAGCGGGTGAGGTGGG | 5708 (SEQ ID NO:6) |
| GGGTTGCCAGTGGGGTGGG | (SEQ ID NO:9) |
| GGNNTGGCGGGTGGGGTGGG | (SEQ ID NO:10) |
| GGGTAGGCGGGTCGGGTGGG | (SEQ ID NO:11) |
| GGGTGGNCGGGTCNGGTGGG | (SEQ ID NO:12) |
| GGGTCGGNNGGTGGGAGGG | (SEQ ID NO:13) |
| GTGTCGGCTGGTGGGGTTGG | (SEQ ID NO:14) |
| GCATCGGCGGGTGGGGTGGG | (SEQ ID NO:15) |
| GGGTAGGCGNNTAGAGTGGG | (SEQ ID NO:16) |
| GGGTCGGCGGGTGGAGTGGG | (SEQ ID NO:17) |
| GGNTCGGGCAGCGGGGTTGG | (SEQ ID NO:18) |
| GGGTCAGCGGNTGTGNNGGG | (SEQ ID NO:19) |
| GGGTCGGCGGGTGGGGTGGG | (SEQ ID NO:5) |
| GGGTCGGCGGGTGGGGTGGG | (SEQ ID NO:5) |
| GGGTCGGCGGGTGGGGTGGG | (SEQ ID NO:5) |
| GGGTCGGCGGGTGGGGTGGG | (SEQ ID NO:5) |

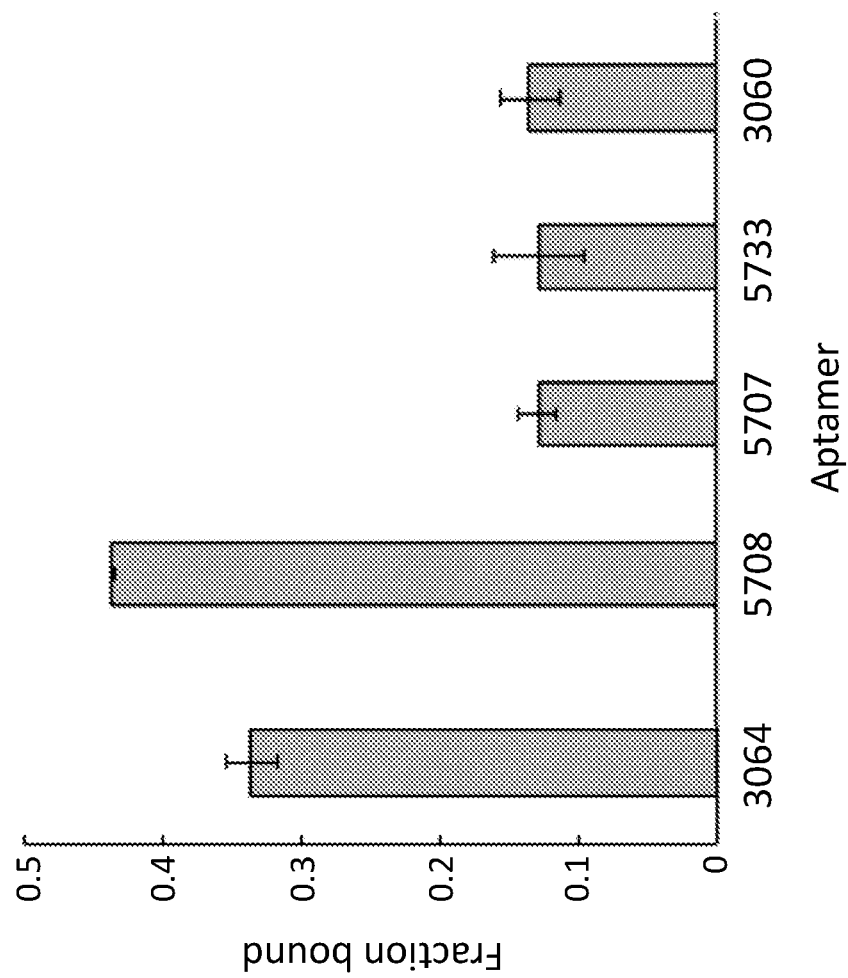

5708
(SEQ ID NO:6)

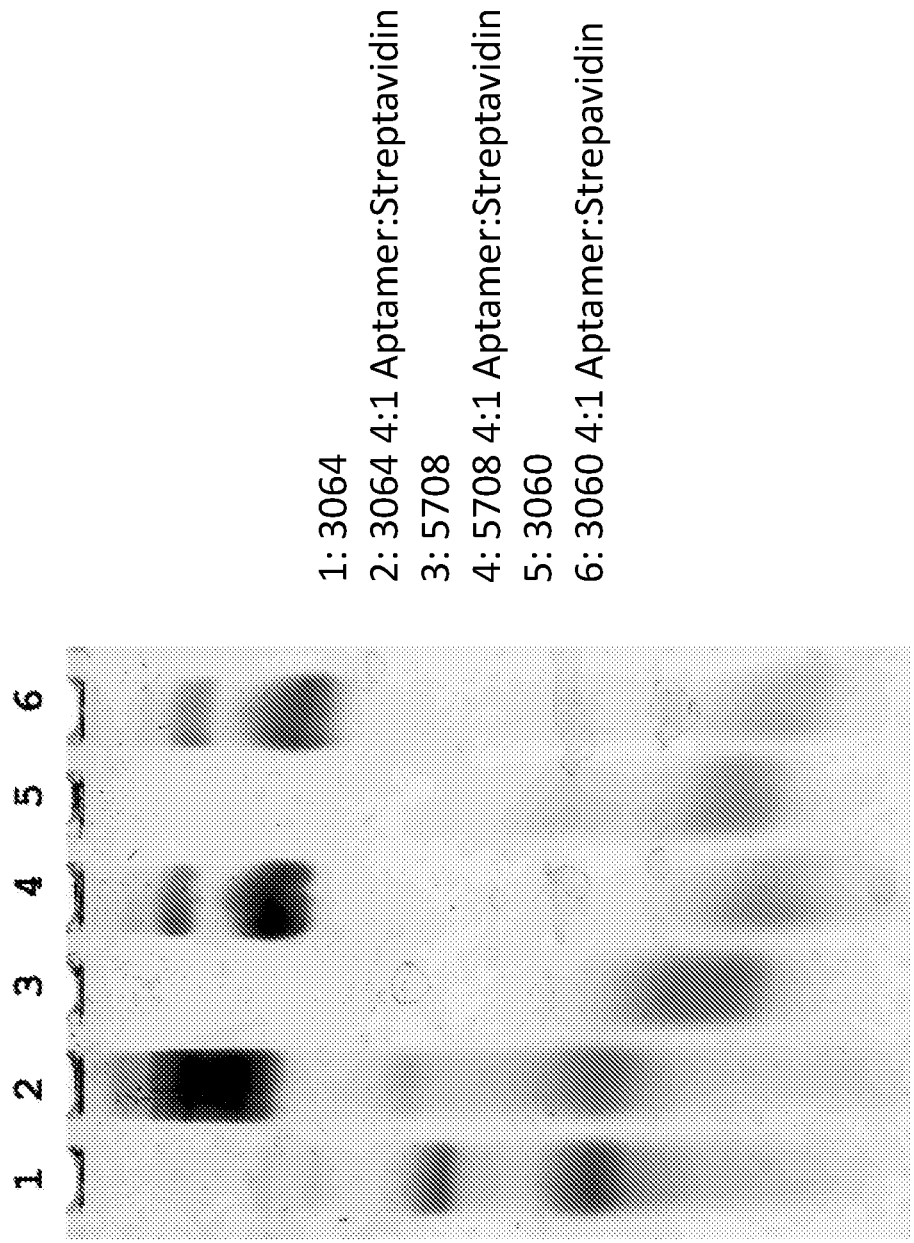

Early oligodendrocytes

Mature oligodendrocytes

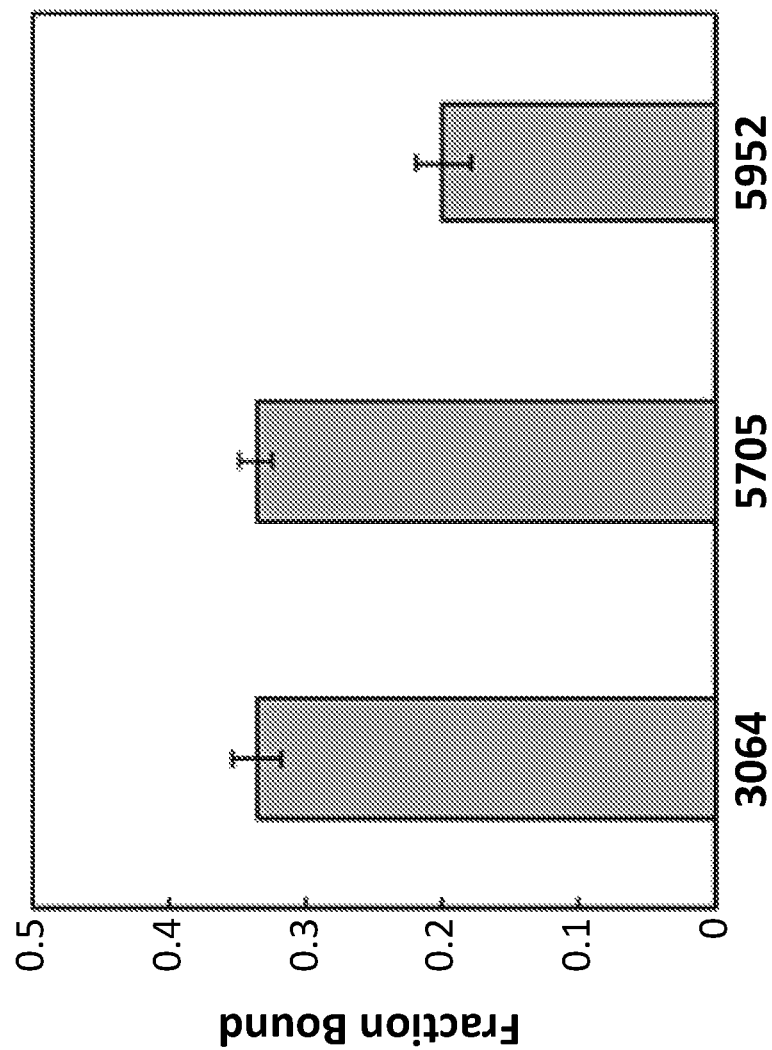

FIG. 11A
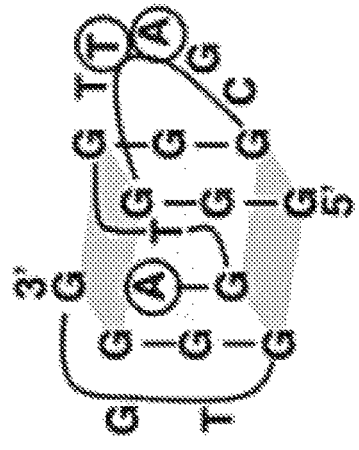
5708
(SEQ ID NO:6)
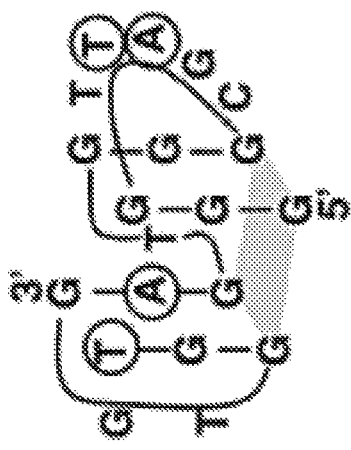
5706
(SEQ ID NO:7)
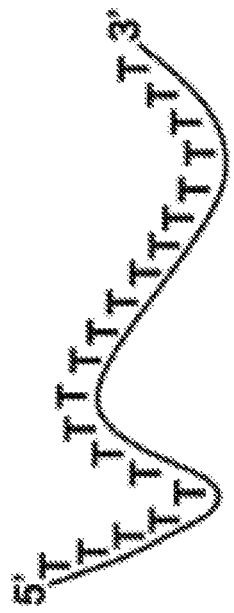
5733
(SEQ ID NO:4)
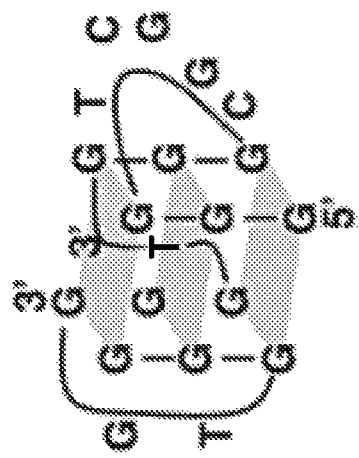
5705
(SEQ ID NO:5)

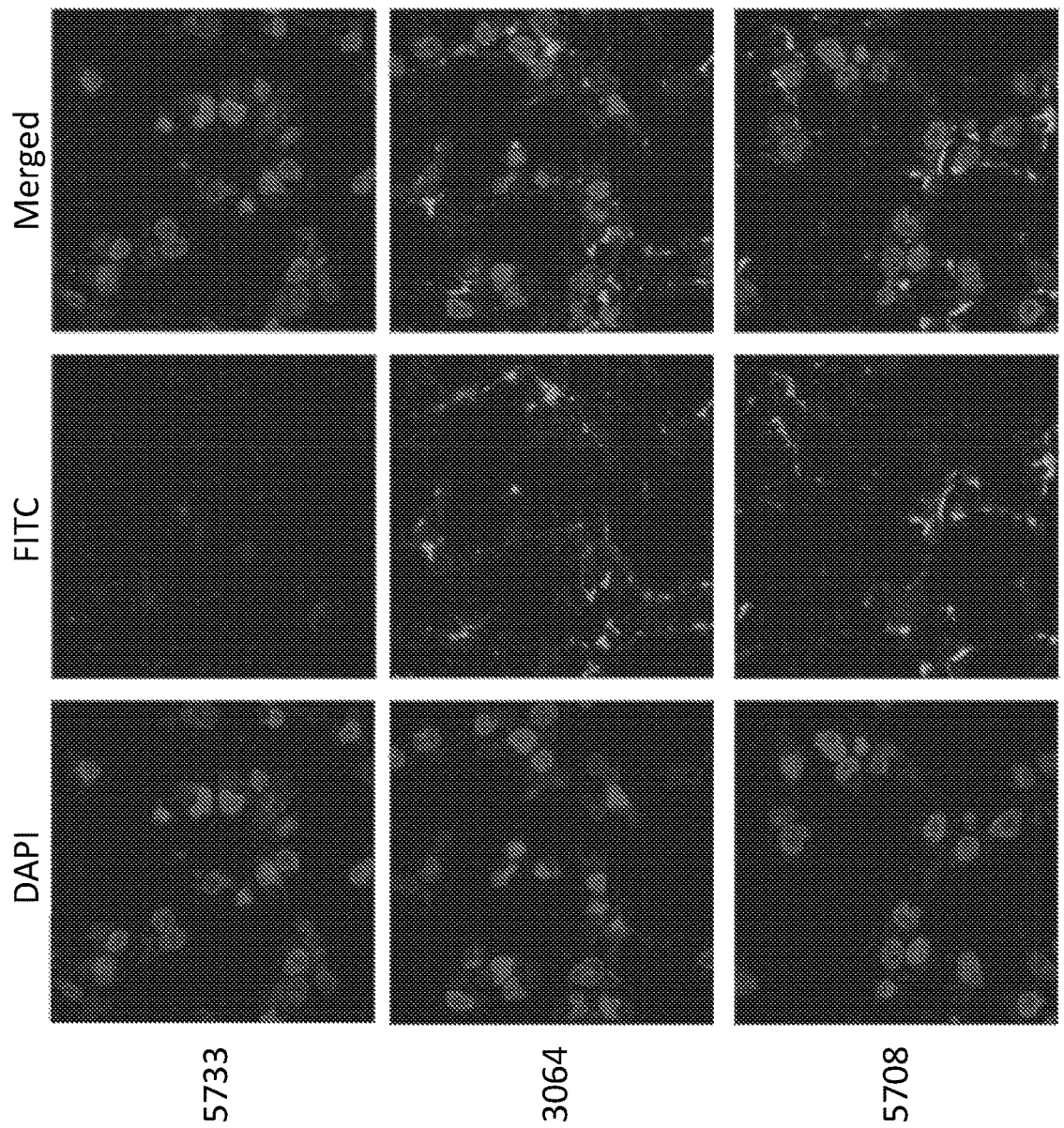

us 12,037,590 B2

SEQUENCE LISTING

<160> NUMBER OF SEQ ID NOS: 25

<210> SEQ ID NO 1
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 1
gggtcggcgg gtggggtggg aggtggtctt gtctctgggt                40

<210> SEQ ID NO 2
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 2
aaagaacaaa aaggataaag ggggagacgg ggggaacatg ggg            43

<210> SEQ ID NO 3
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 3
tttttttttt tttttttttt tttttttttt tttttttttt                40

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
tttttttttt tttttttttt                                      20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
gggtcggcgg gtggggtggg                                      20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
gggttagcgg gtgaggtggg                                      20

<210> SEQ ID NO 7
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 7
gggttagcgg gtgaggtggt                                               20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n is a, c, g, or t

<400> SEQUENCE: 8
gngttagcgg gtggggtgag                                               20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
gggttggcag gtggggtggg                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(4)
<223> OTHER INFORMATION: n is a, c, g, or t

<400> SEQUENCE: 10
ggnntggcgg gtggggtggg                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
gggtaggcgg gtcgggtggg                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
```

<400> SEQUENCE: 12
gggtggncgg gtcnggtggg                                                   20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)..(9)
<223> OTHER INFORMATION: n is a, c, g, or t

<400> SEQUENCE: 13
gggtcggnng gtggggaggg                                                   20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
gtgtcggctg gtggggttgg                                                   20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
gcatcggcgg gtggggtggg                                                   20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(11)
<223> OTHER INFORMATION: n is a, c, g, or t

<400> SEQUENCE: 16
gggtaggcgn ntagagtggg                                                   20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
gggtcggcgg gtggagtggg                                                   20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

```
<220> FEATURE:
<221> NAME/KEY: misc_feature
<222> LOCATION: (3)..(3)
<223> OTHER INFORMATION: n is a, c, g, or t

<400> SEQUENCE: 18
ggntcgggca gcggggttgg                                                    20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t

<400> SEQUENCE: 19
gggtcagcgg ntgtgnnggg                                                    20

<210> SEQ ID NO 20
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 20
agaccagacc agctgatacc agtcgtg                                            27

<210> SEQ ID NO 21
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 21
tacgccaagc cacctgctcc tcctga                                             26

<210> SEQ ID NO 22
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 22
agaccagacc agctgatacc agtcgtg                                            27

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
aaaaaaaaaa aaaaaaaaaa                                                    20

<210> SEQ ID NO 24
```

```
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 24
tcaggaggag caggtggctt ggcgta                                         26

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
aggtggtctt gtctctgggt                                                20
```

SHORT DNA APTAMERS AND METHODS FOR PROMOTING REMYELINATION

CROSS REFERENCE TO RELATED APPLICATIONS

This application is a National Stage application under 35 U.S.C. § 371 of International Application No. PCT/US2019/065010, having an International Filing Date of Dec. 6, 2019, which claims benefit of priority from U.S. Provisional Application No. 62/776,207, filed Dec. 6, 2018. The disclosure of the prior application is considered part of (and is incorporated by reference in) the disclosure of this application.

TECHNICAL FIELD

This document relates to materials and methods for reducing demyelination and promoting remyelination, and particularly short DNA aptamers that can be used to treat demyelinating disease.

BACKGROUND

Multiple sclerosis (MS) is a debilitating inflammatory disease of the central nervous system (CNS), and is characterized by local destruction of the insulating myelin surrounding neuronal axons (Compston and Coles (2002) *Lancet* 359:1221-1231). With more than 200 million MS patients worldwide, there is great need for effective treatments that prevent progression or induce repair. Anti-inflammatory therapies have met with some success in preventing relapses (Bates (2011) *Neurol.* 76:S14-25). In addition, some naturally occurring IgM antibodies identified from human serum can promote both cell signaling and remyelination of CNS lesions in an MS model involving chronic infection of susceptible mice by Theiler's encephalomyelitis virus (TMEV) (Warrington et al. (2000) *Proc. Natl. Acad. Sci. USA* 97:6820-6825) and in the lysolecithin model of focal demyelination (Bieber et al. (2002) Glia 3:241-249).

SUMMARY

This document is based, at least in part, on the identification of a 20-nucleotide, single-stranded DNA aptamer conjugate that has affinity for murine myelin and can promote remyelination in the TMEV model of MS. As described herein, the aptamer can bind to myelin in vitro and in live oligodendrocyte cultures. Peritoneal injection of a formulation containing the aptamer promoted remyelination of CNS lesions in mice infected by Theiler's virus. Interestingly, the DNA aptamer contains guanosine-rich sequences predicted to induce intramolecular folding or intermolecular assembly involving guanosine quartet structures. Relative to monoclonal antibodies, DNA aptamers are small, stable, and non-immunogenic, suggesting new possibilities for MS treatment.

In a first aspect, this document features a method for promoting neuronal remyelination in a mammal in need thereof. The method can include administering to the mammal a pharmaceutical composition containing a nucleic acid aptamer in an amount effective to promote remyelination, where the nucleic acid aptamer includes the sequence set forth in any one of SEQ ID NOS:6 to 19, a fragment of the sequence set forth in any one of SEQ ID NOS:6 to 19, or a variant sequence having at least 90% identity to the sequence of any one of SEQ ID NOS:5 to 19. The nucleic acid aptamer can be a multimer (e.g., a homodimer, homotrimer, or homotetramer). The nucleic acid aptamer can consist essentially of the sequence set forth in any one of SEQ ID NOS:6 to 19. The remyelination can be mediated by central nervous system-type myelin producing cells or by peripheral nervous system-type myelin producing cells. The mammal can be diagnosed with a demyelinating disease (e.g., a demyelinating disease is selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease).

In another aspect, this document features a composition containing a pharmaceutically acceptable carrier and a nucleic acid aptamer that includes the sequence set forth in any one of SEQ ID NOS:6 to 19, a fragment of any one of SEQ ID NOS:6 to 19, or a variant sequence having at least 90% identity to the sequences of any one of SEQ ID NOS:5 to 19. The nucleic acid aptamer can be a multimer (e.g., a homodimer, homotrimer, or homotetramer). The nucleic acid aptamer can consist essentially of the sequence set forth in any one of SEQ ID NOS:6 to 19.

In another aspect, this document features the use of a nucleic acid aptamer in the treatment of a demyelinating disease, where the nucleic acid aptamer contains the sequence set forth in any one of SEQ ID NOS:6 to 19, a fragment of any one of SEQ ID NOS:6 to 19, or a variant sequence having at least 90% identity to the sequences of any one of SEQ ID NOS:5 to 19. The nucleic acid aptamer can consist essentially of the sequence set forth in any one of SEQ ID NOS:6 to 19. The nucleic acid aptamer can be a multimer (e.g., a homodimer, homotrimer, or homotetramer). The demyelinating disease can be selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease.

In still another aspect, this document features the use of a nucleic acid aptamer in the preparation of a medicament for treating a demyelinating disease. The nucleic acid aptamer can contain the sequence set forth in any one of SEQ ID NOS:6 to 19, a fragment of any one of SEQ ID NOS:6 to 19, or a variant sequence having at least 90% identity to the sequences of any one of SEQ ID NOS:5 to 19. The nucleic acid aptamer can consist essentially of the sequence set forth in any one of SEQ ID NOS:6 to 19. The nucleic acid aptamer can be a multimer (e.g., a homodimer, homotrimer, or homotetramer). The demyelinating disease can be selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows the sequences of key aptamers used in the studies described herein, where the aptamers are fluorescently labeled at the 5' end and coupled to biotin at the 3' end. Sequences are shown for the 40-mer G-rich aptamer 3064 (SEQ ID NO:1), negative control aptamer 3060 (SEQ ID NO:2), negative control aptamers 5707 and 5733 (SEQ ID NOS:3 and 4, respectively), the 20-mer "core" sequence within 3064 (also referred to herein as aptamer 5705; SEQ ID NO:5), and the SELEX-optimized aptamer 5708 (SEQ ID NO:6). Nucleotide changes within aptamer 5708 (SEQ ID NO:6), as compared to the "core" sequence of SEQ ID NO:5, are in bold font. It is noted that the 5' fluorescein and 3' biotin components are not essential parts of the myelin-binding sequence, but are simply technical adaptations of the described sequences designed to create fluorescent versions that can be conjugated to proteins related to avidin. FIG. 3B shows the sequences of the 20 most abundant myelin-binding aptamers identified in the SELEX studies. Nucleotide changes as compared to the "core" sequence of SEQ ID NO:5 are in bold font. FIG. 3C is a graph plotting in vitro myelin binding for the indicated aptamer conjugates.

FIG. 5 is an image showing typical aptamer (odd lanes) and streptavidin-aptamer conjugates (even lanes) analyzed by polyacrylamide gel electrophoresis. Aptamers and streptavidin were unlabeled; the gel was stained with SYBR® Gold to visualize the DNA.

FIG. 9B is a graph plotting in vitro myelin binding by streptavidin conjugates with 3' biotinylated 3064, 5705, and 5952.

FIG. 11A is a schematic showing the predicted structures of aptamers of interest. Circled bases in aptamers 5706 and 5708 indicate differences from aptamer 5705.

FIG. 14A is a series of confocal microscopy images of aptamer-streptavidin conjugate binding to human oligodendroglioma (HOG) cells.

DETAILED DESCRIPTION

Figure 1:
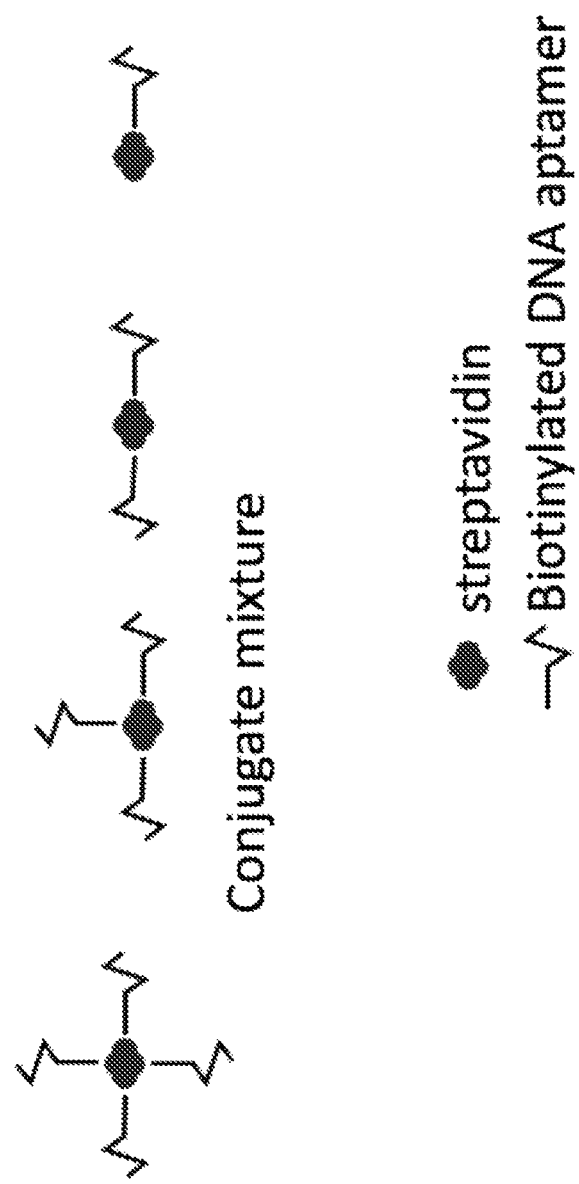
FIG. 1 is a diagram depicting a mixture of biotinylated DNA aptamer conjugates with streptavidin or a comparable protein (e.g., avidin, NeutrAvidin, or other core).

MS is a debilitating neurological disease with a prevalence of about 0.1% in the Western world (Mayr et al. (2003) *Neurol.* 61:1373-1377). MS is fundamentally an inflammatory disease that leads to CNS lesions characterized by the loss of myelin required for electrical insulation of neuronal axons (Noseworthy et al. (2000) *New Engl. J. Med.* (2000) 343:938-952). The resulting symptoms, including fatigue, gait impairment, cognitive impairment, and vision loss, can lead to permanent disability (Rodriguez (1994) *Neurol.* 44:28-33).

While the origin of MS remains unresolved, therapy and cure present even greater challenges. Therapies for relapsing MS include plasma exchange to remove pathogenic immunoglobulins and/or treatment with anti-inflammatory drugs such as glatiramer acetate, β interferon, mitoxantrone, and natalizumab (Bates, supra). These approaches are not curative, and are ineffective in some cases (Freedman (2011) *Neurol.* 76:S26-34). It remains unclear whether curative therapy would best be directed against the immune system, or toward repair and rescue of oligodendrocytes and myelin.

Studies described elsewhere identified multiple natural murine and human IgM autoantibodies that can bind to live cerebellum and cultured oligodendrocytes and promote remyelination in mice (Warrington et al., supra). The target antigens were not known in molecular detail, but the pentavalent character of the IgM antibody appeared to be important for activity (Paz Soldan et al. (2003) *Mol. Cell. Neurosci.* 22:14-24).

This document provides myelin-binding agents that are smaller and more robust than IgM monoclonal antibodies. In particular, as described in the Examples below, an in vitro selection method was used to identify small, single-stranded DNA aptamers that have affinity for myelin and can promote remyelination in mice. Aptamers are folded, single-stranded nucleic acids with activities that, like folded proteins, depend on their three-dimensional shapes and surface features. The advantages of aptamers can, in some embodiments, include one or more of the following: small size, chemical stability, ease of synthesis, lack of immunogenicity, and the availability of in vitro selection technology in which cycles of affinity selection and amplification can be used to identify nucleic acids with rare properties from random libraries that can contain $10^{14}$ or more candidates—chemical diversity exceeding that encoded in mammalian immune systems.

The aptamers and fragments provided herein can be about 10 to about 30 nucleotides in length (e.g., 9, 10, 11, 12, 13, 14, 15, 16, 17, 18, 19, 20, 21, 22, 23, 24, 25, 26, 27, 28, 29, or 30 nucleotides in length, or any range there between). In some cases, an aptamer can contain, consist of, or consist essentially of the sequence set forth in any of SEQ ID NOS:6 to 19, or can contain, consist of, or consist essentially of a fragment of the sequence set forth in any of SEQ ID NOS:6 to 19 (see, FIG. 3B). In some cases, an aptamer can contain, consist of, or consist essentially of a variant of the sequence set forth in any of SEQ ID NOS:5 to 19. A sequence consisting essentially of any of SEQ ID NOS:6 to 19 or a fragment thereof, or a variant of any of SEQ ID NOS:5 to 19, can include, for example, one or more adjunct molecules or sequences (e.g., a chemical or nucleotide sequence spacer at the 5' or 3' terminus that can link the aptamer sequence to a label or tag (e.g., biotin), where the one or more adjunct molecules or sequences do not materially affect the basic and novel characteristics of the aptamer. When a nucleotide sequence spacer is included, the spacer can be from, for example, about three to about 30 nucleotides in length (e.g., three to six, six to nine, nine to 12, 12 to 15, 15 to 18, 18 to 21, 21 to 24, 24 to 27, or 27 to 30 nucleotides in length). Suitable chemical spacers include, for example, various phosphoramidite and (1-dimethoxytrityloxy-propanediol-3-succinoyl)-long chain alkylamino-CPG "spacer modifier" molecules such as those that are commercially available from Glen Research (Sterling, VA).

A fragment of any of SEQ ID NOS:6 to 19 can be 11 to 13, 13 to 15, 15 to 17, or 17 to 19 nucleotides in length. A variant of any of SEQ ID NOS:5 to 19 can include one or more nucleotide substitutions, additions, or deletions as compared to the reference sequences set forth in SEQ ID NOS:5 to 19. In some cases, for example, a variant of any of SEQ ID NOS:5 to 19 can include one to five (e.g., one, two, three, four, five, one to two, two to three, three to four, or four to five) nucleotide substitutions, additions, or deletions as compared to the reference sequences set forth in SEQ ID NOS:5 to 19. Any nucleotide within the reference sequence can be subtracted, and any nucleotide (e.g., any of the four conventional nucleotides or any nucleotide derivative) can be added to or substituted within the reference sequence.

In some cases, a variant of any of SEQ ID NOS:5 to 19 can have a nucleotide sequence that is at least 90% identical (e.g., 90% or 95% identical), but less than 100% identical, to the reference sequences set forth in SEQ ID NOS:5 to 19. The percent sequence identity between a particular nucleic acid sequence and a sequence referenced by a particular sequence identification number is determined as follows. First, a nucleic acid sequence is compared to the sequence set forth in a particular sequence identification number using the BLAST 2 Sequences (B12seq) program from the stand-alone version of BLASTZ containing BLASTN version 2.0.14. This stand-alone version of BLASTZ can be obtained online at fr.com/blast or at ncbi.nlm.nih.gov. Instructions explaining how to use the B12seq program can be found in the readme file accompanying BLASTZ. B12seq performs a comparison between two sequences using the BLASTN algorithm, which is used to compare nucleic acid sequences. (BLASTP, also included in BLASTZ, is used to compare amino acid sequences.) To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\B12seq c:\seq1.txt -j c:\seq2.txt -p blastn -o c:\output.txt -q -1 -r 2. If the two compared sequences do not share homology, then the designated output file will not present aligned sequences.

Once aligned, the number of matches is determined by counting the number of positions where an identical nucleotide is presented in both sequences. The percent sequence identity is determined by dividing the number of matches either by the length of the sequence set forth in the identified sequence (e.g., SEQ ID NO:6), or by an articulated length (e.g., 100 consecutive nucleotides from a sequence set forth in an identified sequence), followed by multiplying the resulting value by 100. For example, an amino acid sequence that has 19 matches when aligned with the sequence set forth in SEQ ID NO:6 is 95.0 percent identical to the sequence set forth in SEQ ID NO:6 (i.e., 19/20× 100=95.0). It is noted that the percent sequence identity value is rounded to the nearest tenth. For example, 75.11, 75.12, 75.13, and 75.14 is rounded down to 75.1, while 75.15, 75.16, 7.17, 75.18, and 7.19 is rounded up to 7.2. It also is noted that the length value will always be an integer.

An "isolated" nucleic acid molecule is a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a donor nucleic acid sequence can be mutated using standard techniques, including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992.

A nucleic acid aptamer can be monomeric or can be multimeric. For example, an aptamer can be a dimer, a trimer, a tetramer, a pentamer, or a hexamer, and can be homomeric or heteromeric. In some embodiments, an aptamer can be configured as a homomultimer. See, for example, the Examples below, which describe the use of a homotetramer containing four copies of SEQ ID NO:6. In some cases, an aptamer can be complexed with another compound that can provide stabilization and/or multimerization. For example, one or more aptamers can be combined using biotin-streptavidin linkages (as described in the Examples) or comparable linkages (e.g., biotin-avidin or biotin-NeutrAvidin linkages), or with polyethylene glycol linkages (see, e.g., Govan et al. (2011) *Bioconjugate Chem.* 22(10):2136-2142). In some embodiments, aptamer synthesis can be performed with a solid support to yield structures in which the aptamers are head-to-head multimers. Synthesis reagents are available commercially (e.g., from Glen Research; Sterling, VA); see, also Shchepinov (1999) *The Glen Report* 12(1):1-4, available on the World Wide Web at glenresearch.com/GlenReports/GR12-11.html and glenresearch.com/GlenReports/GR12-1.pdf. Further, azide/alkyne 3+2 cycloaddition chemistry can allow for rapid coupling of derivatized oligonucleotides to a central chemical backbone. Such a procedure could be used to create oligonucleotide multimers cleanly and efficiently without a central protein. See, e.g., Rostovtsev et al. (2002) *Angew Chem. Int. Ed.* 41:2596-2599; and Huisgen (1963) *Angew Chem. Int. Ed.* 2:565-598, as well as *The Glen Report* (2008) 20(1):8-9 available on the World Wide Web at glenresearch.com/GlenReports/GR20-14.html and glenresearch.com/GlenReports/GR20-1.pdf. See, also, U.S. Publication No. 2009/0234105; Alleti et al. (2010) *J. Org. Chem.* 75(17):5895-5903; and Yim et al. (2010) *J. Med. Chem.* 53(10):3944-3953.

The aptamers described herein can be used to treat demyelinating diseases (e.g., MS) by inducing remyelination or reducing demyelination. For example, a nucleic acid aptamer as described herein (e.g., an aptamer containing the sequence set forth in SEQ ID NO:6 or a variant or fragment thereof) can be synthesized and formulated into a pharmaceutical composition for administration to a subject (e.g., a mammal) diagnosed as having a disorder of the nervous system in which the myelin sheath of neurons is damaged. In addition to MS, demyelinating diseases that can affect the central nervous system include idiopathic inflammatory demyelinating diseases, transverse myelitis, Devic's disease progressive multifocal leukoencephalopathy, optic neuritis, and leukodystrophies and acute disseminated encephalomyelitis (ADEM). Demyelinating diseases that can affect the peripheral nervous system include Guillain-Barré syndrome, chronic inflammatory demyelinating polyneuropathy, anti-MAG peripheral neuropathy, and Charcot-Marie-Tooth disease.

The aptamers described herein can be incorporated into compositions for administration to a mammal in need thereof (e.g., a mammal identified as having a demyelinating disease). Thus, this document provides, for example, the use of aptamers as described herein in the manufacture of medicaments for treating (e.g., reducing) demyelination and/or enhancing remyelination.

Methods for formulating and subsequently administering therapeutic compositions are well known to those skilled in the art. Dosages typically are dependent on the responsiveness of the mammal to the compound, with the course of treatment lasting from several days to several months, or until a suitable response is achieved.

Persons of ordinary skill in the art routinely determine optimum dosages, dosing methodologies and repetition rates. Optimum dosages can vary depending on the relative potency of an aptamer, and generally can be estimated based on the $EC_{50}$ found to be effective in in vitro and/or in vivo animal models. Compositions containing the aptamers may be given once or more daily, weekly, monthly, or even less often, or can be administered continuously for a period of time (e.g., hours, days, or weeks). For example, an aptamer or a composition containing an aptamer can be administered to a patient at a dose of at least about 0.01 ng/kg to about 100 mg/kg of body mass.

An aptamer can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain an aptamer as provided herein in combination with a pharmaceutically acceptable carrier. Pharmaceutically acceptable carriers include, for example, pharmaceutically acceptable solvents, suspending agents, or any other pharmacologically inert vehicles for delivering nucleic acid aptamers to a subject (e.g., a mammal). Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing aptamers as described herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful. Methods and compositions for transdermal delivery include those described in the art (e.g., in Wermeling et al. (2008) *Proc. Natl. Acad. Sci. USA* 105:2058-2063; Goebel and Neubert (2008) *Skin Pharmacol. Physiol.* 21:3-9; Banga (2007) *Pharm. Res.* 24:1357-1359; Malik et al. (2007) *Curr. Drug Deliv.* 4:141-151; and Prausnitz (2006) *Nat. Biotechnol.* 24:416-417).

Nasal preparations can be presented in a liquid form or as a dry product. Nebulized aqueous suspensions or solutions can include carriers or excipients to adjust pH and/or tonicity.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions provided herein can contain any pharmaceutically acceptable salts, esters, or salts of such esters, or any other compound which, upon administration to a subject, is capable of providing (directly or indirectly) the biologically active aptamer. The term "pharmaceutically acceptable salts" refers to physiologically and pharmaceutically acceptable salts of the nucleic acid aptamers useful in methods provided herein (i.e., salts that retain the desired biological activity of the parent aptamers without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions.

In some cases, an aptamer provided herein can be formulated as a sustained release dosage form. For example, an aptamer can be formulated into a controlled release formulation. In some cases, coatings, envelopes, or protective matrices can be formulated to contain one or more of the polypeptides provided herein. Such coatings, envelopes, and protective matrices can be used to coat indwelling devices such as stents, catheters, and peritoneal dialysis tubing. In some cases, an aptamer provided herein can be incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association an active ingredient (e.g., an aptamer or an aptamer conjugate) with the desired pharmaceutical carrier(s). Typically, the formulations can be prepared by uniformly and intimately bringing the active ingredient(s) into association with liquid carriers or finely divided solid carriers or both, and then, if necessary, shaping the product. Formulations can be sterilized if desired, provided that the method of sterilization does not interfere with the effectiveness of the molecules(s) contained in the formulation.

The nucleic acid aptamers (e.g., SEQ ID NOS:5 to 19, or fragments or variants thereof) provided herein can be administered to a subject (e.g., a mammal, such as a human, non-human primate, mouse, rat, dog, cat, rabbit, sheep, cow, horse, or pig) in order to reduce demyelination that can occur with diseases such as MS, for example. The aptamers can be administered at any suitable dose, depending on various factors including, without limitation, the agent chosen and the patient characteristics. Administration can be local or systemic.

In some embodiments, an aptamer or a composition containing an aptamer can be administered at a dose of at least about 0.01 ng/kg to about 100 mg/kg of body mass (e.g., about 10 ng/kg to about 50 mg/kg, about 20 ng/kg to about 10 mg/kg, about 0.1 ng/kg to about 20 ng/kg, about 3 ng/kg to about 10 ng/kg, or about 50 ng/kg to about 100 µg/kg) of body mass, although other dosages also may provide beneficial results.

The methods provided herein can include administering to a mammal an effective amount of an aptamer, or an effective amount of a composition containing such an aptamer. As used herein, the term "effective amount" is an amount of an aptamer or aptamer-containing composition that is sufficient to reduce the occurrence of demyelination or increase the occurrence of remyelination in a mammalian recipient by at least 10% (e.g., 10%, 15%, 20%, 25%, 30%, 40%, 50%, 60%, 70%, 75%, 80%, 85%, 90%, 95%, 99%, or 100%). The presence or extent of demyelination and remyelination can be evaluated using any suitable method, including, for example, the methods described in the following Examples section.

In some embodiments, for example, an "effective amount" of an aptamer as provided herein can be an amount that reduces demyelination in a treated mammal by at least 10% as compared to the level of demyelination in the mammal prior to administration of the aptamer, or as compared to the level of demyelination in a control, untreated mammal.

The invention will be further described in the following examples, which do not limit the scope of the invention described in the claims.

EXAMPLES

Optimization of a 40-Mer Antimyelin DNA Aptamer Identifies a 20-Mer with Enhanced Properties for Potential MS Therapy Example 1

Materials and Methods

SELEX for Optimization: A "core" 20-mer (GGGTCGGCGGGTGGGGTGGG; SEQ ID NO:5) derived from a 40-mer aptamer (designated 3064) was synthesized by Integrated DNA Technologies (Coralville, IA) with 85:5:5:5 mixing of each base at each position. SELEX was then performed using a protocol based on methods described elsewhere (Nastasijevic et al., PLoS ONE, 7:e39595, 2012). The modified library was heated in PBS for 1 minute at 90° C., followed by 15 minutes of cooling on ice and 8 minutes of cooling at room temperature. 200 µL (10 µg) of murine myelin (Nastasijevic et al., supra) was pelleted and washed twice in 500 µL binding buffer (20 mM Tris-HCl, pH 7.6, 10 mM NaCl, 0.5 mM KCl). The pellet was then resuspended in binding buffer and combined with aptamer at a final concentration of 1 µM aptamer in a total volume of 100 µL. The mixture was incubated at 37° C. for 30 minutes with rotation to mix. Myelin was again pelleted and washed twice in 1 mL binding buffer to remove aptamers that were not bound to myelin. Bound aptamers were then recovered by phenol/chloroform extraction following a wash in 400 µL 2× proteinase K buffer. This method was repeated for five rounds, using 100× by mass sheared salmon sperm DNA as a competitor in rounds three to five. After the fifth round of selection, recovered aptamers were ligated into the pGEM®-Teasy cloning vector (Promega; Madison, WI), which were then cloned and sequenced.

Twenty recovered sequences were analyzed. As compared to the "core" 20-mer (SEQ ID NO:5), the most common base changes were: C to T at base 5, G to A at base 6, G to A at base 14, and G to T at base 20. Five of the 20 clones (25%) contained the base changes from CG to TA at bases 5 and 6. The optimized sequence (5708) discussed further below included the C to T at base 5, G to A at base 6, and G to A at base 14.

Myelin Binding Assay: Myelin binding of the aptamers was quantified as described elsewhere (Heider et al., Molecular Therapy: Methods & Clinical Development, 9:270-277, 2018) with freshly prepared murine myelin. Aptamers used in the assay were synthesized (Integrated DNA Technologies) with a 3' biotin tag and 5' 6-FAM. Labelled aptamers were conjugated to streptavidin by incubation of a 4:1 molar mixture of aptamer:streptavidin at 37° C. for 1 hour with mixing.

A final concentration of 230 nM of aptamer was combined with 0.2 µg/µL murine myelin. Sheared salmon sperm DNA was used in 20-fold excess by mass as a competitor for nonspecific binding of DNA to myelin. A final sample volume of 100 µL was incubated at 37° C. for 90 minutes, which was followed by a 1 minute centrifugation step to pellet myelin and bound DNA. Supernatant was allocated to a new tube and the pellet was then washed twice in 100 µL PBS. Each supernatant recovered after washing was combined with the original recovered supernatant. The pellet was then resuspended once more into 300 µL PBS so that the volume of myelin-DNA suspensions and recovered supernatants were equal. These two samples were read by a plate reader to determine the 6-FAM signal in each, and to quantify the fraction of signal bound to myelin.

Circular Dichroism-Spectroscopy: CD-spectroscopy confirmation of G-quadruplex structures was performed. Solutions of 4 µM aptamer were prepared for spectroscopy in various salt buffers, and heated for 5 minutes at 90° C. This was followed by a 30 minute cooling period at room temperature before spectra were quantified. Blank spectra for each buffer solution were collected as background measurements that were subtracted from sample readings.

Remyelination Assay in TMEV Mice: Mice were sacrificed and perfused with 4% paraformaldehyde. Each spinal cord was removed from the spinal column and flash frozen in liquid nitrogen. Spinal cords were cut into 10 1-2 mm blocks and then placed on end for cutting cross sections of the spinal cord. Tissue was stained with Luxol Fast Blue, which stains normal myelin dark blue. Lesions were characterized by the absence of blue staining (demyelination). Remyelinated lesions were characterized by thin myelin sheaths that stain by Luxol Fast Blue as very light blue. All analyses were done "blinded" with all slides de-identified and coded. After all slides were scored, the slides were identified by groups and the data were expressed for remyelination as the percentage of lesions that showed remyelination. Each of those points was graphed and statistical comparisons were done relative to control group 3060 by one way Student's T test, as the data were normally distributed.

Results

The work described herein led to the identification of an optimized DNA aptamer derivative that, when conjugated to streptavidin, showed enhanced binding to murine myelin in vitro, a result shown to be predictive of remyelination activity in the mouse TMEV model of MS (Heider et al., supra). Work described elsewhere (see, Nastasijevic et al., supra; Smestad and Maher, (2013) *Nucleic Acids Res.* 41:1329-1342; and Perwein et al., (2018) *Expert Opin. Biol. Ther.* 18(5):545-560) was based on a 40-nucleotide G-rich DNA aptamer (3064; SEQ ID NO:1) selected in vitro for affinity to crude murine myelin. When terminally biotinylated and conjugated with streptavidin, that mixture of multivalent complexes (FIG. 1) showed remyelination activity in the mouse TMEV model.

Figure 2:
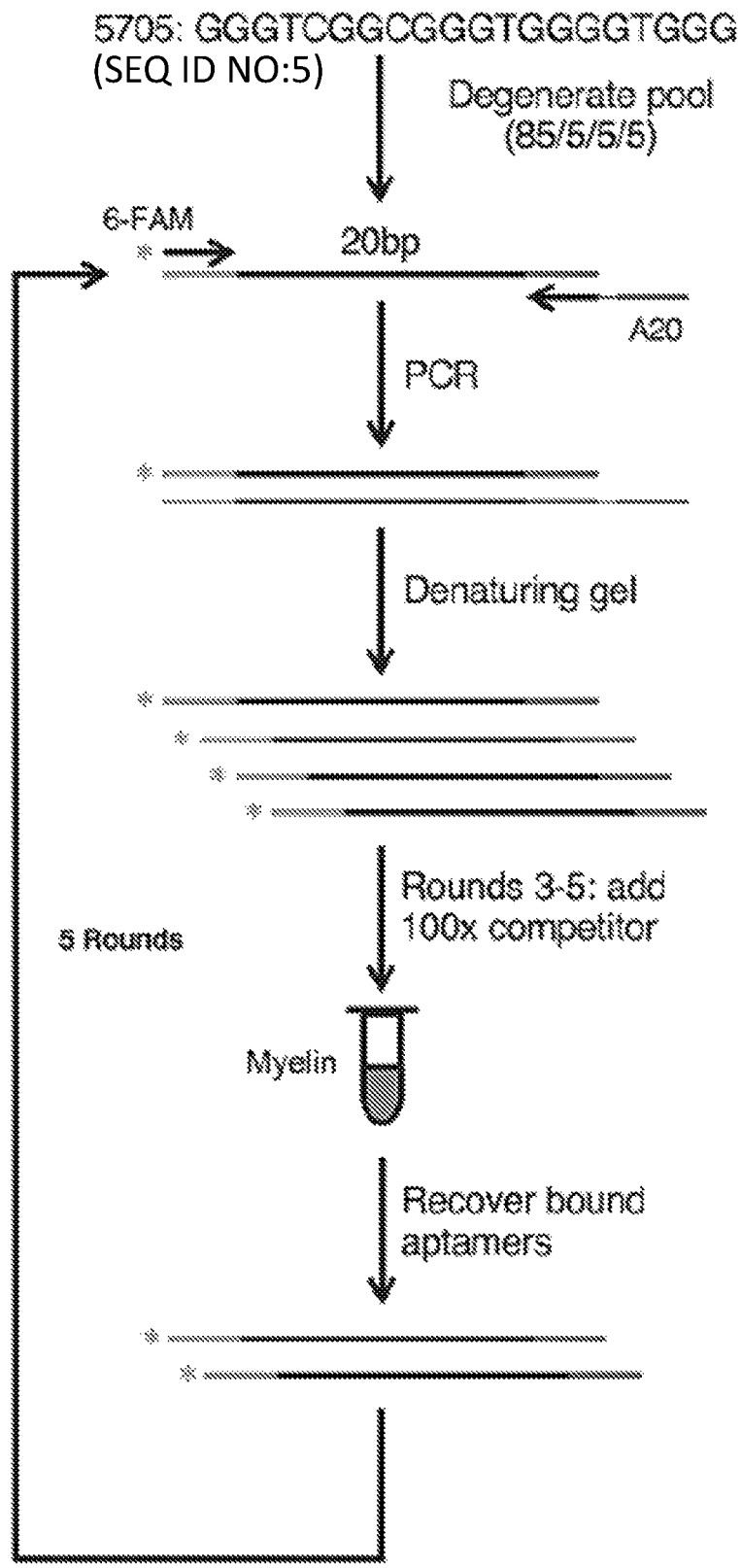
FIG. 2 is a diagram showing the steps in a Systematic Evolution of Ligands by EXponential enrichment (SELEX) method for identifying optimal sequences for short, myelin-binding DNA aptamers.
Figure 4A:
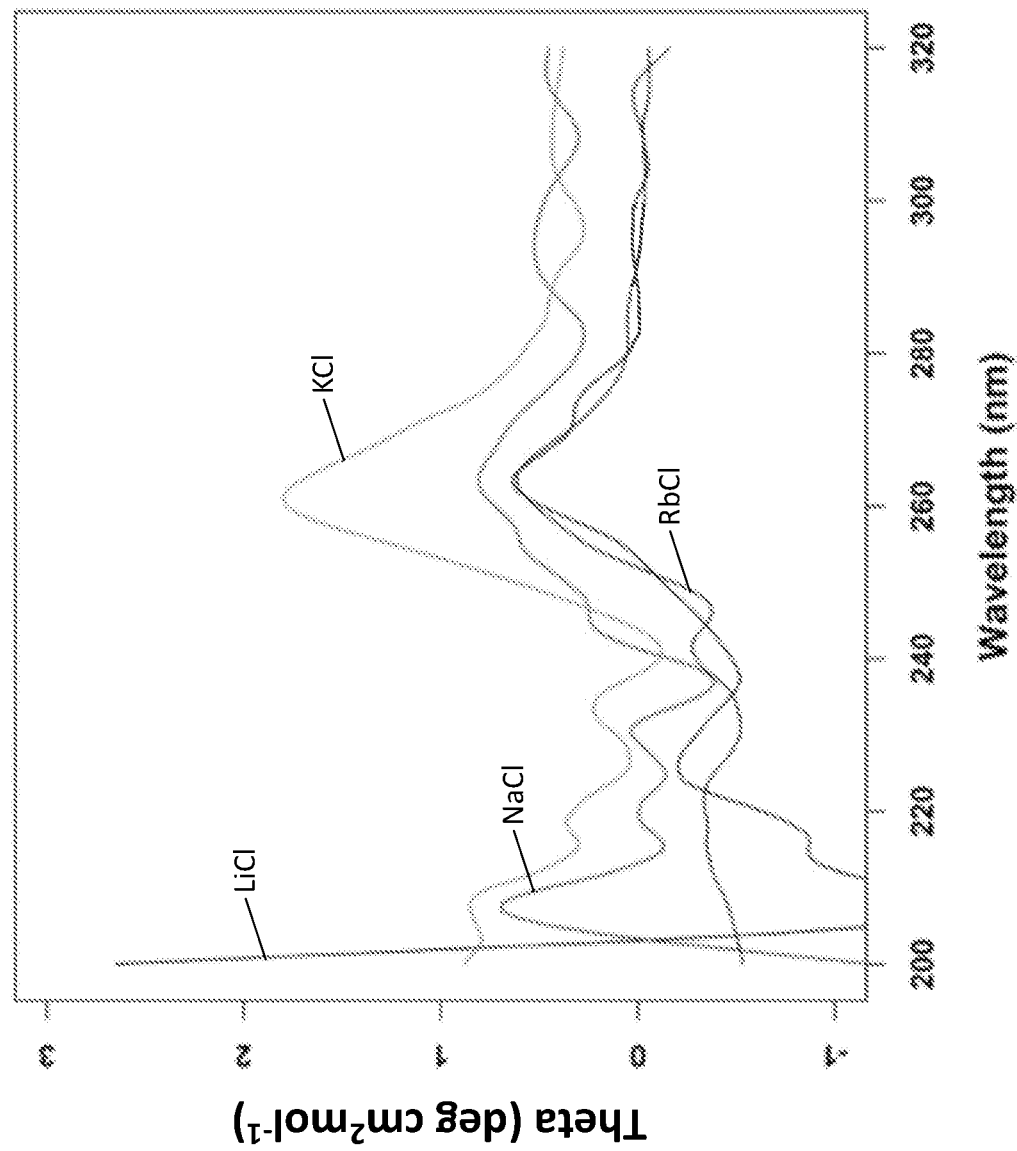
FIGS. 4A-4C are circular dichroism (CD) spectra for the 5708 aptamer at a concentration of 50 µM in different salt buffers (FIGS. 4A and 4B), and the 5078 or 3064 aptamer in streptavidin-conjugated or unconjugated form in 160 mM KCl (FIG. 4C).
Figure 4B:
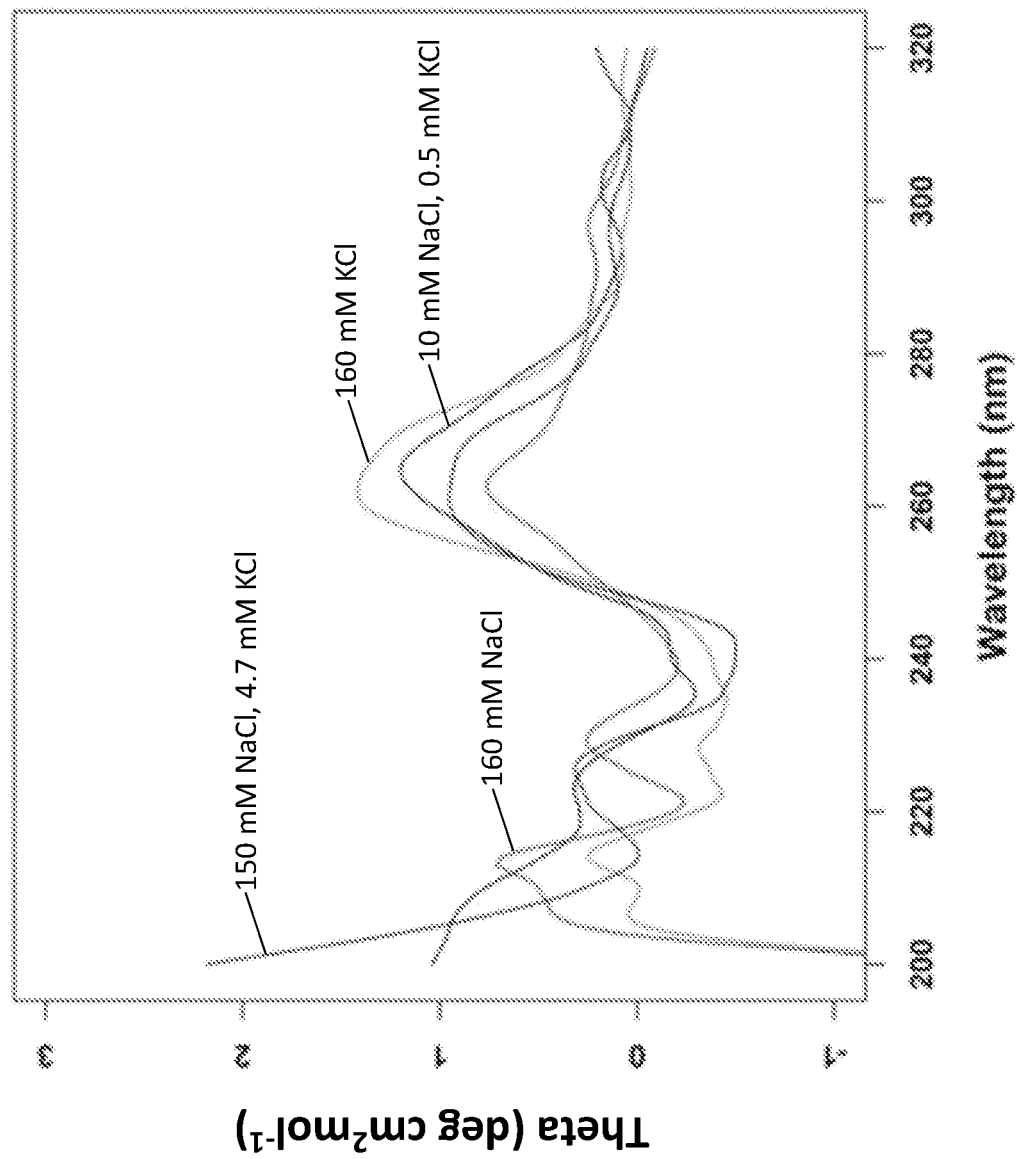
Figure 4C:
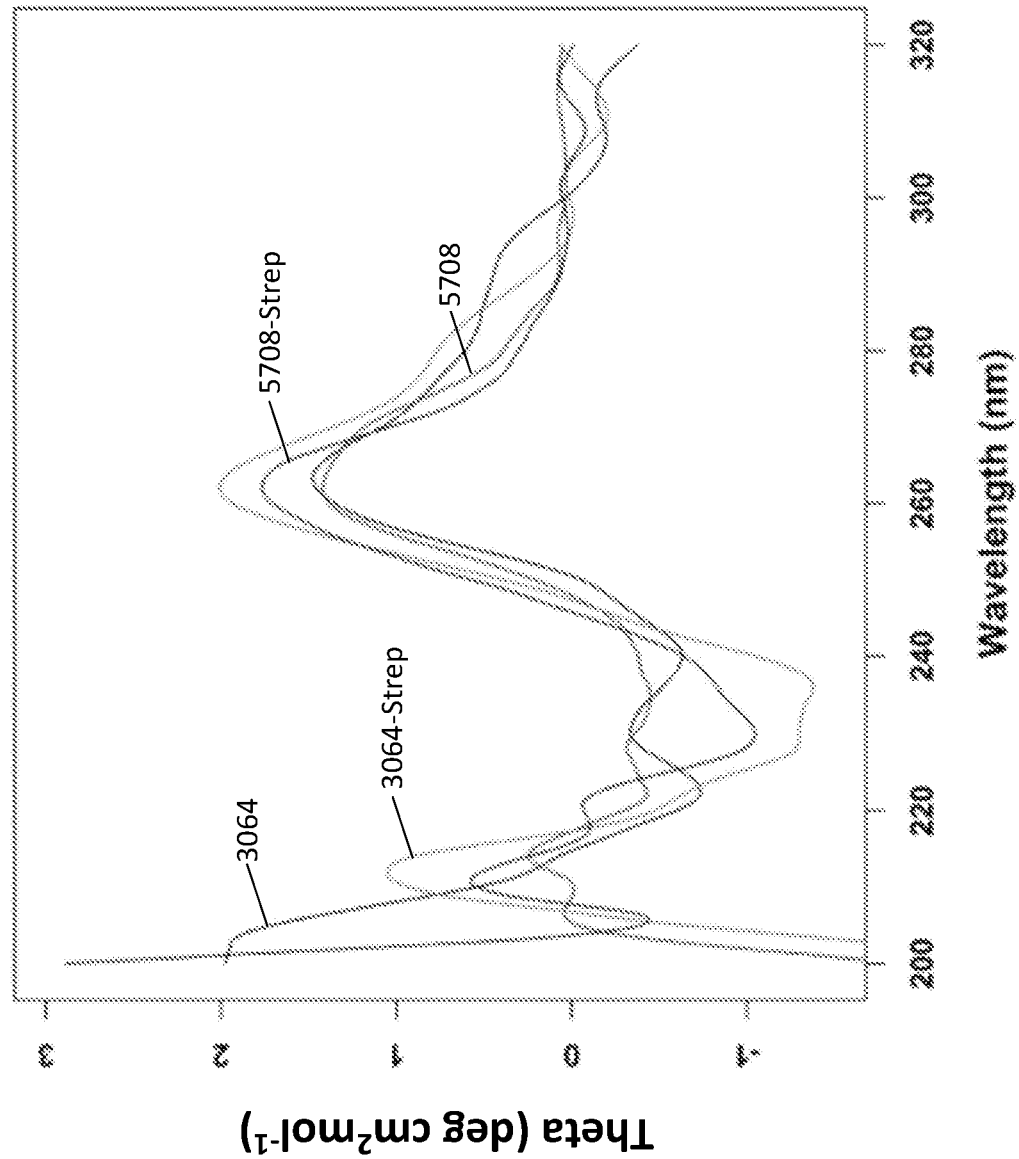
Figure 4D:
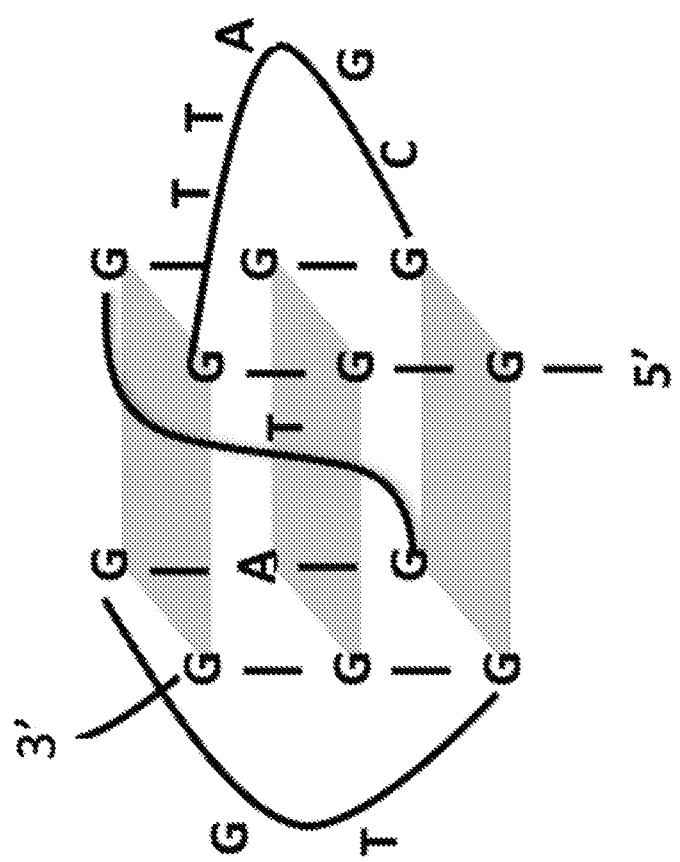
FIG. 4D is a diagram depicting the G-quadruplex structure into which aptamer 5708 is predicted to fold. The schematic of the folded G-quadruplex reflects the parallel-stranded fold type that is believed to be predominant at physiologic ion concentrations, but it is to be noted that the aptamer exists in a state of structural equilibrium that can be influenced by, for example, ion concentrations, temperature, and accessibility to its cognate binding partner in myelin.

Sub-sequences within 3064 and SELEX-optimized sub-sequences derived from 3064 were tested for myelin binding activity. The G-rich half of the 3064 sequence showed the best myelin binding activity in vitro. This sequence was further made degenerate using SELEX, and re-selected for myelin binding activity in vitro (FIG. 2). The most active fraction of sequences was cloned and sequenced. Derivatives with improved binding activity were deduced and a particular variant, designated 5708 (SEQ ID NO:6), was compared with other derivatives and controls (FIGS. 3A and 3B) in the myelin binding assay. Streptavidin conjugates of 5708 bound myelin more tightly than any other aptamers tested (FIG. 3C).

CD spectroscopy showed that aptamer 5708 appeared to fold into a G-quadruplex structure, reminiscent of the structure of 3064 (Smestad and Maher, supra) (FIGS. 4A-4D). An analysis of the mixture of conjugates obtained when biotinylated 5708 was coupled 4:1 with streptavidin showed some heterogeneity, as observed with previous aptamer conjugations (FIG. 5).

Figure 6A:
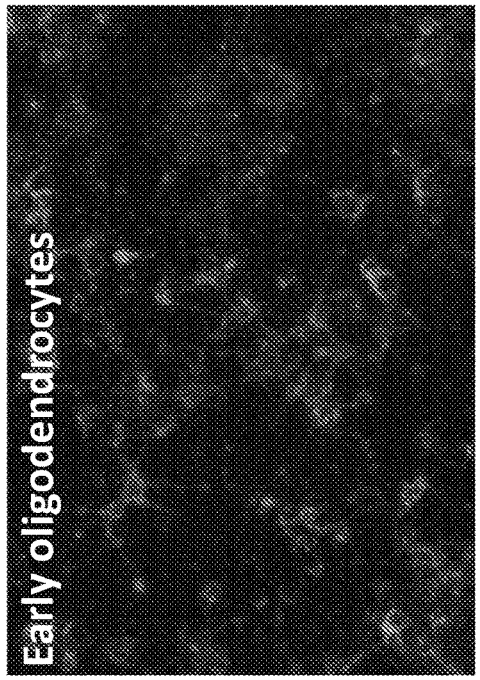
FIGS. 6A-6D are a series of images showing cultured mouse oligodendrocyte cells incubated with aptamer 3064 (FIGS. 6A and 6B) or aptamer 5708 (FIGS. 6C and 6D). The aptamers were detected by addition of a labeled aptamer-binding protein (FIGS. 6A and 6C). The cells also were labeled by addition of an oligodendrocyte marker (FIGS. 6B and 6D).
Figure 6B:
Figure 6C:
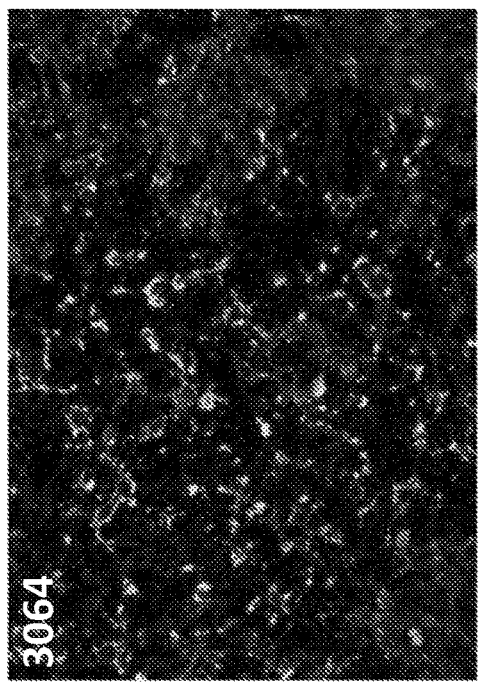
Figure 6D:

Aptamers 3064 and 5708 were then shown to bind living mouse oligodendrocytes. To evaluate the aptamer complex binding specificity, nervous system cells from the brains of mice were established in culture. Aptamers were added to media and allowed to bind, followed by a labeled protein that recognized the aptamer. Cells also were labeled with markers of oligodendrocytes. While 3064 bound to myelinating cells early in their maturation sequence (FIGS. 6A and 6B), 5708 bound best to cells later in maturation (FIGS. 6C and 6D). These differences in character may contribute to the ability of the aptamer to induce remyelination in vivo.

Figure 7:
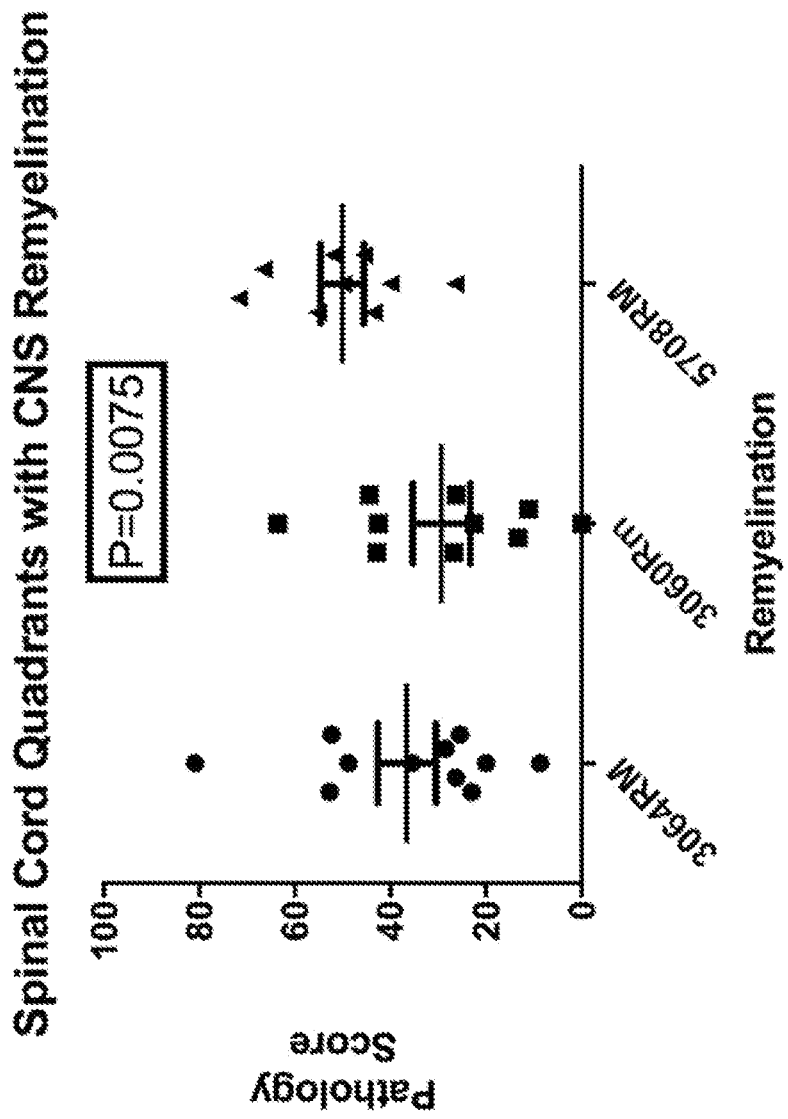
FIG. 7 is a graph plotting pathology scores (percentage of spinal cord quadrants showing remyelination) for TMEV-infected mice that were treated with streptavidin-conjugated aptamer 3064, aptamer 5708, or negative control aptamer 3060.

In light of its improved myelin binding activity, aptamer 5708 was biotinylated and conjugated to streptavidin. Ten (10) i.p. doses (twice per week for 5 weeks) of this formulation, or conjugates of aptamer 3064 or negative control 3060, were administered to TMEV-infected mice to monitor provoked remyelination. Blinded pathology scoring was conducted. In this study, aptamer 5708 showed induced remyelination that was statistically greater than either 3064 or the negative control (FIG. 7).

Example 2

Materials and Methods

Optimization SELEX: A degenerate SELEX library based upon the 20-nucleotide minimal antimyelin aptamer designated 5705 (GGGTCGGCGGGTGGGGTGGG; SEQ ID NO:5) was synthesized by Integrated DNA Technologies with 15% nucleotide randomization at each position, flanked by 5' (AGACCAGACCAGCTGATACCAGTC GTG; SEQ ID NO:20) and 3' (TACGCCAAGC-CACCTGCTCCTCCTGA; SEQ ID NO:21) regions used for PCR amplification using forward primer 5'-FAM-AGACCAG ACCAGCTGATACCAGTCGTG-3' (SEQ ID NO:22) and reverse primer 5'-AAAAAAAAAAAAAAAAAAAA-spacer18-spacer18-TCAGGAGGAGCAGGTG GCTTGGCGTA-3' (SEQ ID NO:23-spacer18-spacer18-SEQ ID NO:24). Optimization SELEX was then performed according to a protocol described elsewhere (Nastasijevic et al., supra) with slight modification. The degenerate library (300 nmol) was heated in phosphate-buffered saline (PBS) for 1 minute at 90° C., followed by snap cooling on ice and equilibration at room temperature. Two hundred microliters (10 mg) of murine myelin was pelleted and washed twice in 500 mL binding buffer (145 mM NaCl, 4 mM KCl, 1.5 mM $CaCl_2$, 10 mM $Na_3PO_4$). The pelleted material was then suspended in binding buffer and combined with aptamer (1 mM final concentration) in 100 mL total volume. This mixture was incubated at 37° C. for 30 minutes with rotary mixing. Myelin was again pelleted by centrifugation at 4,700 g and washed twice in 1 mL binding buffer to remove any unbound sequences. Remaining bound aptamers were recovered by solubilization of myelin in 400 mL 2× proteinase K buffer [200 mM Tris-HCl, pH 7.6, 2.5 mM ethylenediaminetetraacetic acid (EDTA), 300 mM NaCl, and 2% sodium dodecyl sulfate] and subsequent phenol/chloroform extraction. This method was repeated over five rounds. Beginning with the third round, nonspecific competitor DNA (100× sheared and denatured salmon testes DNA by mass) was introduced to increase stringency of selection conditions. After five rounds of selection, recovered aptamers were PCR amplified, ligated into the pGEM-Teasy cloning vector, and cloned into DH5a cells. Colonies were grown, plasmids were isolated, and aptamer sequences were determined by Sanger sequencing.

Myelin-binding assay: Aptamer binding to myelin suspensions in vitro was performed as described elsewhere (Heider et al., supra) with freshly prepared murine myelin (Nastasijevic et al., supra). Aptamers used in the assay were synthesized (Integrated DNA Technologies) with 3' biotin and 5' 6-FAM labels. Labeled aptamers were conjugated to streptavidin by incubation of a 4:1 molar mixture of aptamer: streptavidin with 0.25 mM aptamer at 37° C. for 1 hour with mixing in PBS supplemented with 1 mM $MgCl_2$. Aptamer 3060 (AAAGAACAAAAAGGATAAAGGGG-GAGACGG GGGGAACATGGGG; SEQ ID NO:2), a known G-quadruplex forming molecule, was used as a negative control.

A final concentration of 230 nM aptamer was combined with 0.2 mg/mL murine myelin. Sheared salmon sperm DNA was used in 20-fold excess by mass as a competitor for nonspecific DNA binding to myelin. A final sample volume of 100 mL was incubated at 37° C. for 90 minutes, followed by a 1 minute microcentrifugation step to pellet myelin and bound DNA. The supernatant was allocated to a new tube and the pellet was then washed twice with 100 mL PBS. Aliquots of recovered supernatant were combined. The pellet was then resuspended once more in 300 mL PBS so that the volumes of myelin-DNA suspensions and recovered supernatants were equal. Fluorescence in these paired samples was read in a black 96-well microplate (Greiner Bio-One) using a plate reader (Analyst AD 96-384) to determine the 6-FAM signal and calculate the fraction of signal bound to myelin in each sample.

Figure 8:
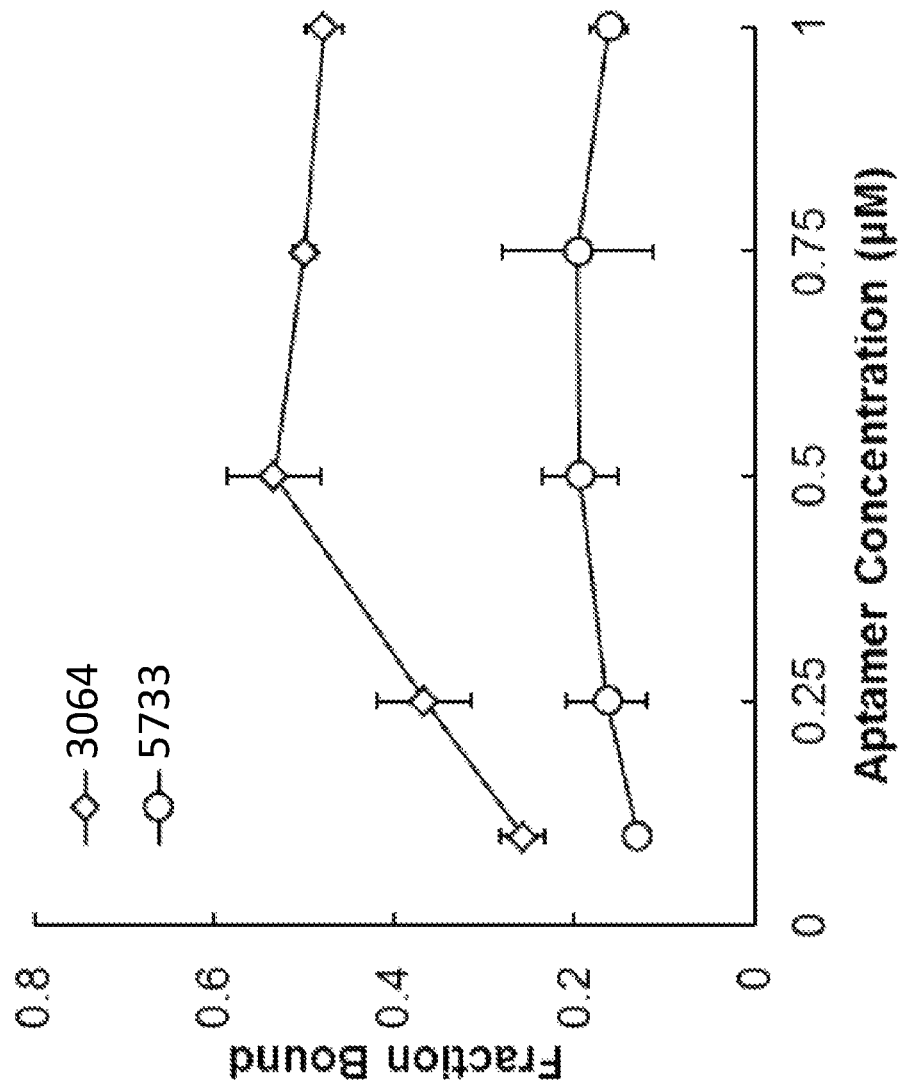
FIG. 8 is a graph plotting myelin binding of aptamers 3064 and 5733 under standard myelin binding assay conditions.

The concentration of aptamer used in this assay was determined based on data published elsewhere (Heider et al., supra) and a myelin-binding curve comparing binding of parent molecule 3064 and negative control 5733 (FIG. 8). Based on these data, the aptamer concentration used was appropriate for comparison, since positive control binding was significantly greater than binding of the negative control but was below the point of saturation of myelin binding.

Circular dichroism spectroscopy: CD spectroscopy for analysis of G-quadruplex structures was performed using a JASCO J-810 Spectropolarimeter. Solutions of 4 mM aptamer in 160 mM KCl were heated for 5 minutes at 90° C., followed by snap cooling on ice and an equilibration period at room temperature before spectra were recorded. Blank spectra for the buffer solution and unconjugated streptavidin in buffer were collected as background measurements that were subtracted from relevant sample readings.

Gel mobility analysis of G-quadruplex structures: Aptamers were diluted to a final concentration of 4 mM in a buffer containing 10 mM phosphate and 12.5 mM LiCl, NaCl, KCl, or RbCl. Aptamer solutions were heated at 90° C. for 5 minutes, followed by snap cooling on ice and equilibration at room temperature. Samples were supplemented with loading buffer (Thermo Scientific; R0611) and loaded onto 12% 29:1 acrylamide:bisacylamide gels with 0.5× Trisborate EDTA running buffer containing 12.5 mM of the same salt solution used for sample preparation. Electrophoresis was carried out for 2.5 hours at 300V (13 V/cm) at room temperature. Images were collected on a Typhoon fluorescence imaging system after SYBR Green I post-stain.

HOG cell-binding assay in culture: Aptamers (1 mM) were conjugated with fluorescein isothiocyanate (FITC)-labeled streptavidin in a 4:1 ratio as described above. HOG cells were grown at 37° C. in Dulbecco's modified Eagle medium (DMEM) with supplemented 10% fetal bovine serum (FBS) and Pen/Strep antibiotics (P/S). Culture conditions were controlled at 5% $CO_2$, 21% $O_2$, and 90% humidity. Aptamer conjugates were added to cells at a final concentration of 1 mM aptamer each in 1 mL fresh DMEM with FBS and P/S. Exposure was for 2 hours under standard culture conditions, followed by fixation for 20 minutes using 10-fold diluted formaldehyde solution (Sigma; 252549). Fixed cells were stained with 4',6-diamidino-2-phenylindole (DAPI) (Roche; 10236276001) for 7 minutes and washed twice with PBS. Images were collected on a Zeiss LSM 780 microscope using an autofocus routine to capture an optimal image plane based on DAPI channel intensity.

Fluorescence quantitation was performed using an automated image analysis process in CellProfiler. The area of a cell was defined by first selecting nuclei on a DAPI channel image, then expanding all selections by an identical number of pixels in all directions to approximate the space filled by a single cell. FITC channel intensity was then summed over the entire space of each identified cell. This measurement was compared between treatment conditions.

HOG cell-binding assay by flow cytometry: HOG cells were plated into six-well plates at 30% confluence. Fluorescently labeled oligonucleotide conjugates were prepared by mixing 3'-biotinylated oligonucleotides with FITC-labeled streptavidin (Invitrogen; SA1001) in a 4:1 stoichiometric ratio in PBS containing 1 mM $MgCl_2$, incubating at 37° C. for 30 minutes, and storing at 4° C. until use. The next day, the medium was aspirated from HOG cells in plates and replaced with 1 mL of fresh medium supplemented with FITC-labeled oligonucleotide-streptavidin complexes at 250 nM final streptavidin concentration. Plates were replaced in the 37° C. incubator for 2 hours before aspirating the medium, scraping the cells into 1 mL fresh medium, and collecting the cells by centrifugation at 500 g for 5 minutes at 4° C. Cells were resuspended in 500 mL PBS, placed on ice, and then analyzed by flow cytometry to quantify cell-associated FITC fluorescence.

Results

Figure 9A:
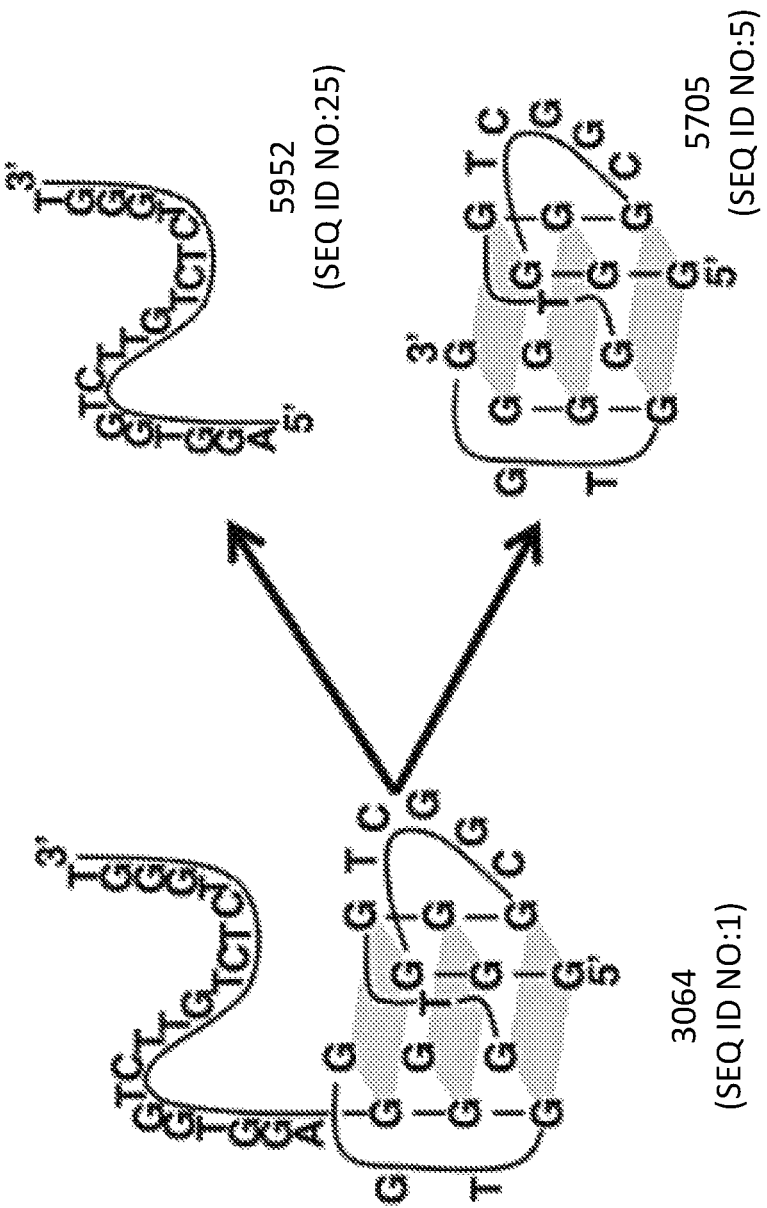
FIG. 9A shows the predicted structure of the 40-nucleotide antimyelin DNA aptamer 3064 (SEQ ID NO:1) and the 20-nucleotide derivatives 5952 (SEQ ID NO:25) and 5705 (SEQ ID NO:5).

Myelin binding of twenty-nucleotide 3064 derivatives: 3064 was identified as a strong myelin-binding 40-nucleotide DNA aptamer with a distinct 5' G-quadruplex-forming half and an unstructured 3' half (see, e.g., Example 1 above, and Smestad and Maher, supra). Studies were conducted to test the hypothesis that the myelin-binding activity of 3064 is conferred by the 5' G-quadruplex-forming half (FIG. 9A). Biotinylated 20-nucleotide derivatives were synthesized as individual DNA oligonucleotides designated 5705 (the 5' G-quadruplex-forming half; SEQ ID NO:5) and 5952 (the 3' unstructured half; SEQ ID NO:25) and formulated as streptavidin conjugates using a 4:1 aptamer: streptavidin ratio. Using an in vitro myelin-binding assay shown to predict in vivo remyelinating activity in mice (Heider et al., supra), 5705 exhibited myelin binding equivalent to parent aptamer 3064. In contrast, 5952 exhibited less myelin binding (FIG. 9B).

Although 5952 binds myelin weakly, this 20 nucleotide sequence does not increase binding of 5705 relative to 3064. and was therefore not included in the optimization studies. This result confirmed that the 20 5' G-quadruplex forming nucleotides of 3064 are active in myelin binding.

Optimization of aptamer LJM-5705 results in improved myelin binding: Studies were then conducted to assess whether sequence modifications within the 20-nucleotide guanosine-rich aptamer 5705 could yield enhanced myelin-binding properties. A SELEX strategy similar to that described elsewhere (Nastasijevic et al., supra) was used to optimize the sequence of 5705. The approach involved synthesis of a lightly randomized degenerate SELEX library derived from the 5705 sequence, with a 15% probability of base randomization at each nucleotide position (FIG. 2). Through iterative selection of this library for binding to suspensions of crude murine myelin in vitro and recovery of bound sequences in each cycle, the best myelin-binding molecules emerged. These optimized DNAs included sequences that outperformed the parental aptamer for myelin-binding capabilities. In rounds 3-5 of SELEX, a 100-fold mass excess of sheared and denatured salmon sperm DNA was added as a competitor for nonspecific DNA-binding activity. After five rounds, the recovered pool was sequenced, and candidate optimized antimyelin aptamers were identified (FIG. 3B).

Figure 10A:
FIG. 10A is a diagram illustrating MEME motif analysis of recovered sequences.
Figure 10B:
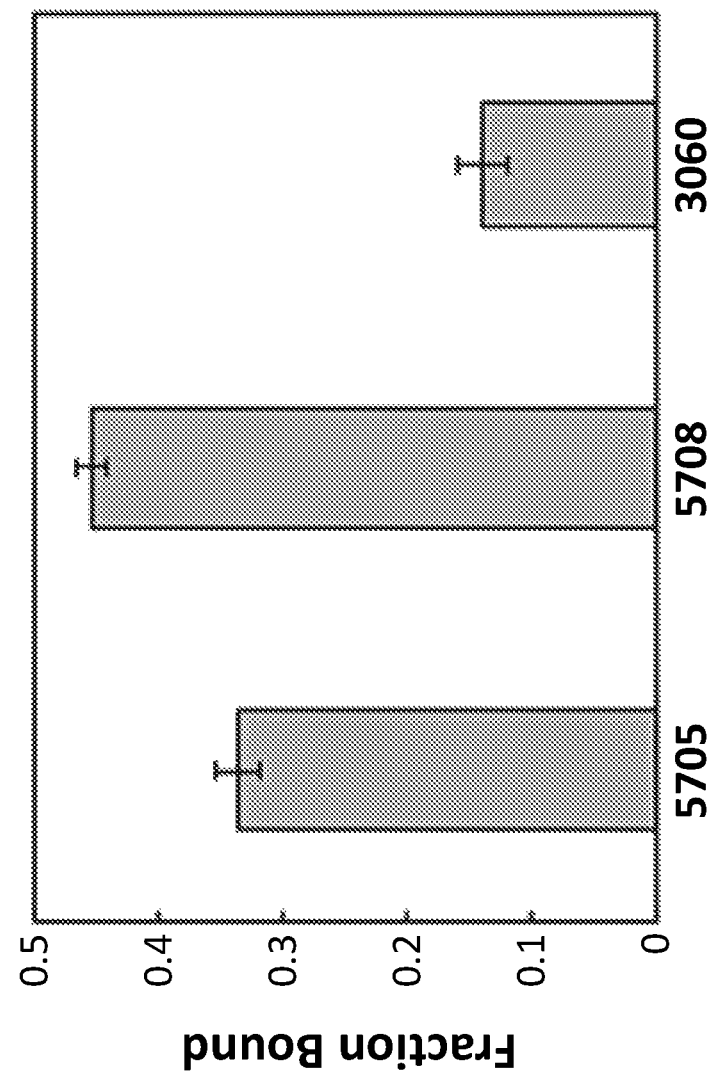
FIG. 10B is a graph plotting the myelin binding properties of streptavidin conjugates of 3'-biotinylated aptamers 5705, 5708, and 3060.

MEME motif analysis (Bailey and Elkan (1994) Proc Second Int Conf Intell Syst Mol Biol 1:28-36) of the recovered pool indicated that bases involved in predicted G-quadruplex formation were highly conserved among the recovered molecules, but the loop regions separating guanosine-rich sequences displayed higher mutation frequency (FIG. 10A). It is notable that 12/20 sequences showed a switch from C to another base at the fifth position, with transition to thymidine being the most common (7/12). Similarly, 6/20 sequences contained a change at the sixth position, exclusively mutating to adenine. In addition, 5/20 bases differed at the 14th position, with a strong preference for adenine (4/5). Each of these changes is predicted to alter loops separating G-tetrad stacks, likely impacting binding properties without perturbing of the core G-quadruplex. One of the optimized molecules, designated 5708 (SEQ ID NO:6), was selected for further in vitro testing to assess myelin binding properties. Analysis was carried out with a myelin-binding assay (Heider et al., supra). Comparing 20-nucleotide 5708 to the parental 20-nucleotide aptamer 5705 (SEQ ID NO:5), a statistically significant enhancement in myelin binding was observed for 5708 (FIG. 10B). This suggested that the SELEX approach was successful in identifying a variant with improved binding to the crude myelin suspension.

Figure 11B:
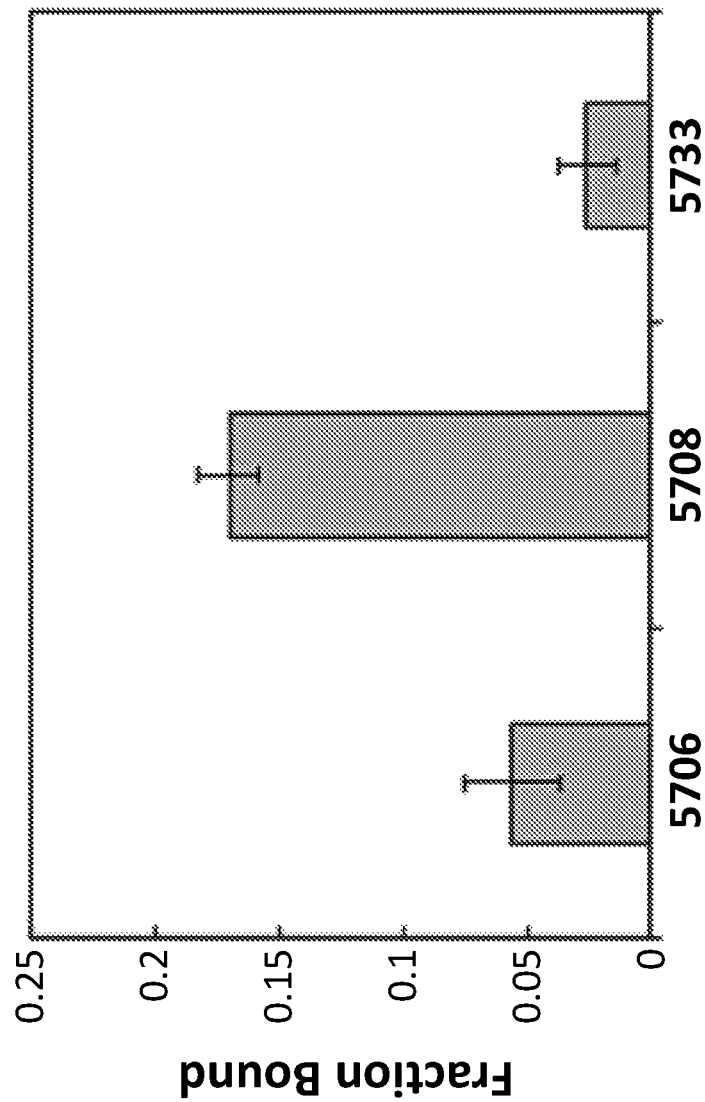
FIG. 11B is a graph plotting the fraction of each biotinylated aptamer bound as a streptavidin conjugate in a myelin-binding assay.

G-quadruplex structure is essential for myelin-binding activity: Among the variants identified by optimization SELEX was 5706, which was identical to 5708 except for mutation of the 3' terminal guanine nucleotide to thymine (FIG. 11A). Because this position is predicted to participate in a G-tetrad, this result raised the possibility that an incomplete G-quadruplex structure might be tolerated for myelin binding. However, 5706 displayed very low myelin-binding capacity compared to 5708 (FIG. 11B). This suggested that the loss of G-quadruplex formation can disable myelin binding.

Figure 11C:
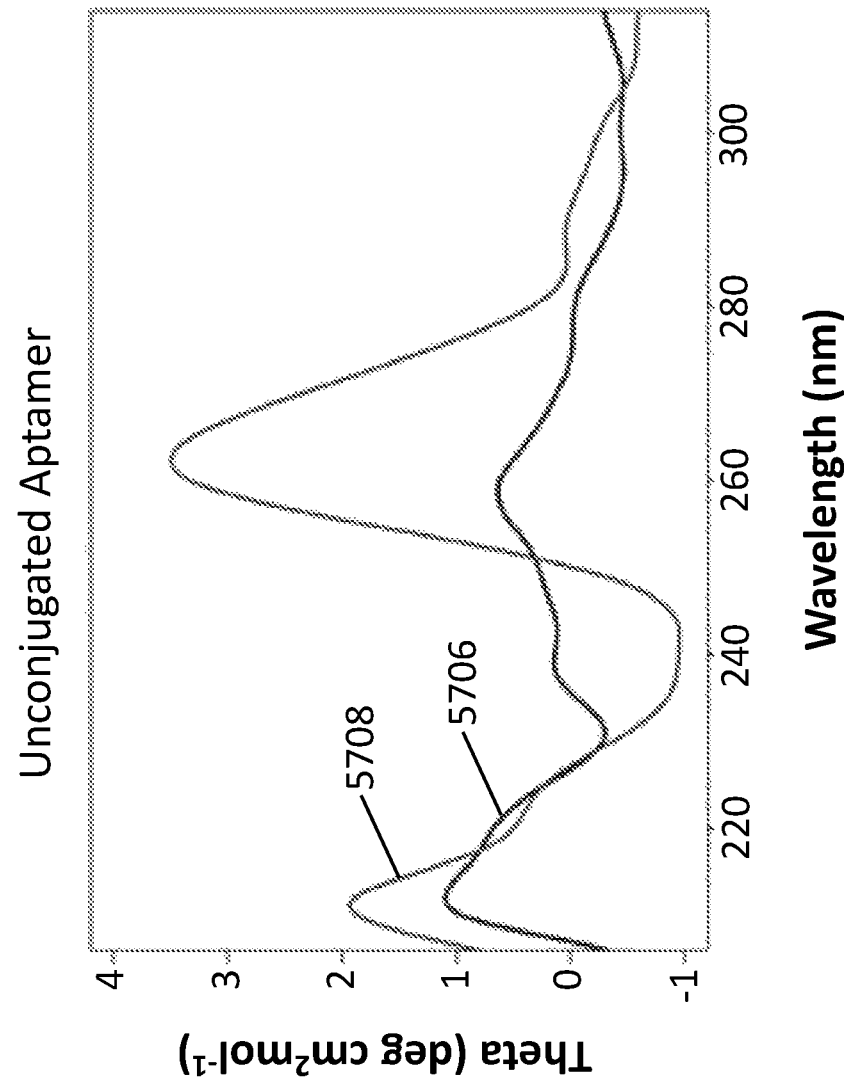
FIG. 11C is a graph plotting CD spectra of folded 5706 and 5708 aptamers in solution.

G-quadruplex formation by 5708 (active) and 5706 (inactive) was further characterized. CD spectroscopy confirmed that 5708 forms a parallel-stranded G-quadruplex in phosphate buffer supplemented with 160 mM KCl, indicated by a positive peak in molar ellipticity at 260 nm and a negative peak at 240 nm (FIG. 11C and TABLE 1) (Villar-guerra et al., *Angew Chem Int Ed Engl* 57:7171-7175).

Figure 11D:
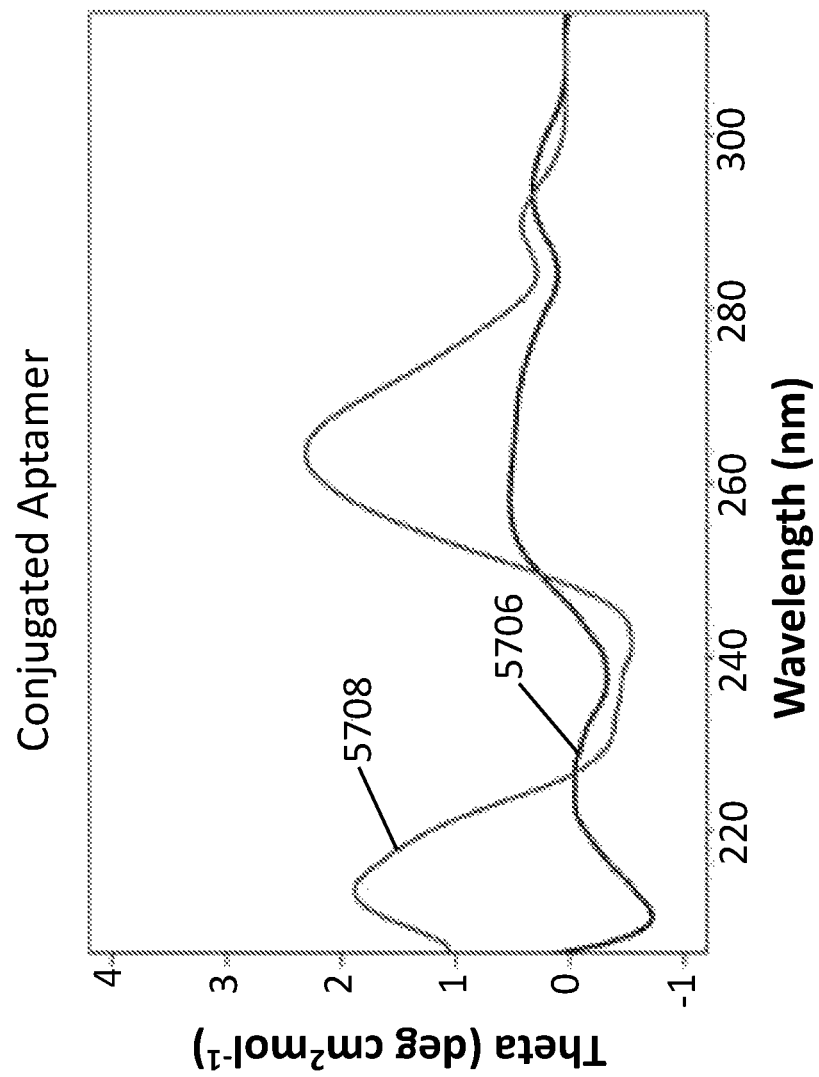
FIG. 11D is a graph plotting CD spectra of folded biotinylated 5706 and 5708 conjugated to streptavidin (CD spectra of streptavidin subtracted).
Figure 12A:
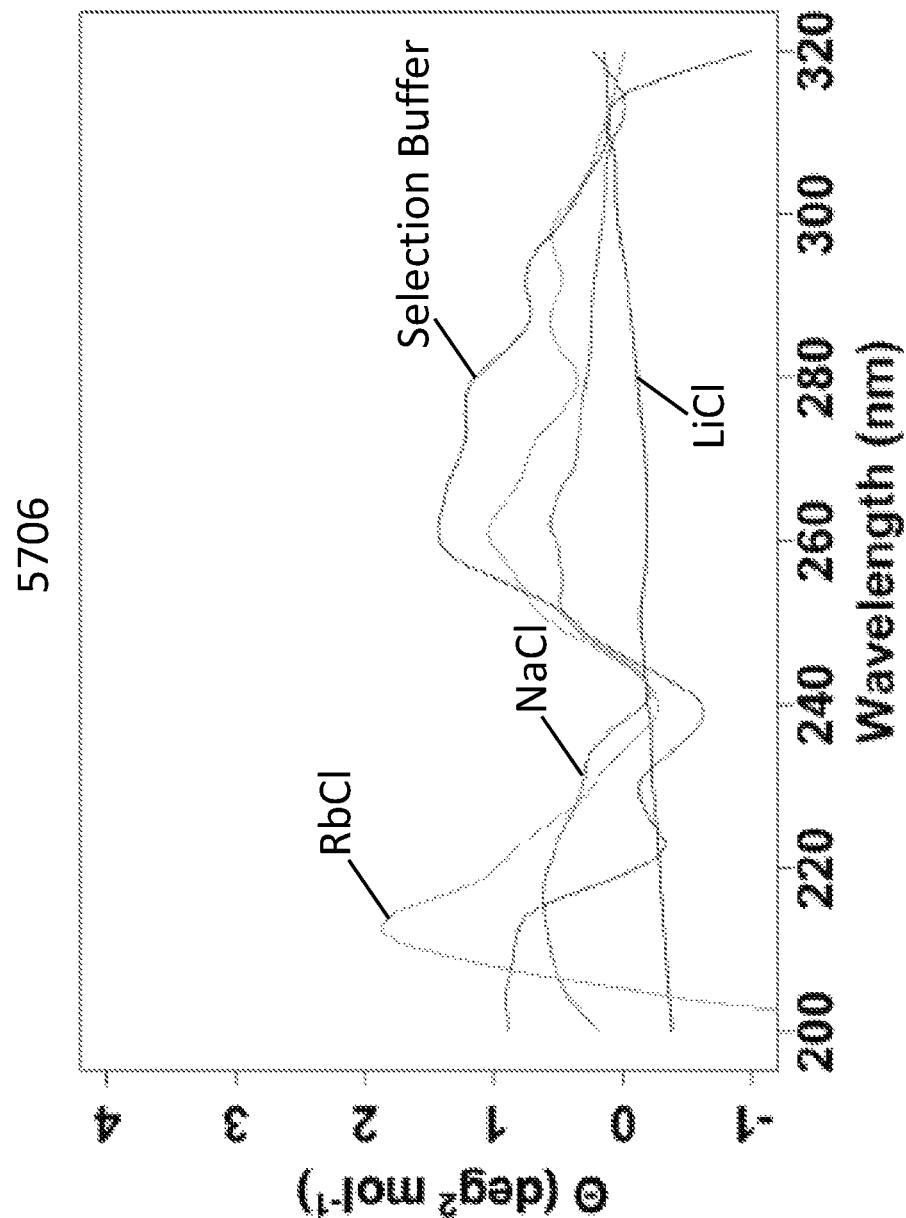
FIGS. 12A and 12B are graphs plotting CD spectroscopy analysis of folded 5706 (FIG. 12A) and 5708 (FIG. 12B) in 160 mM $Li^+$, $Na^+$, $Rb^+$, or selection buffer, which revealed that aptamer 5708 forms a stable G-quadruplex in optimization SELEX conditions.
Figure 12B:
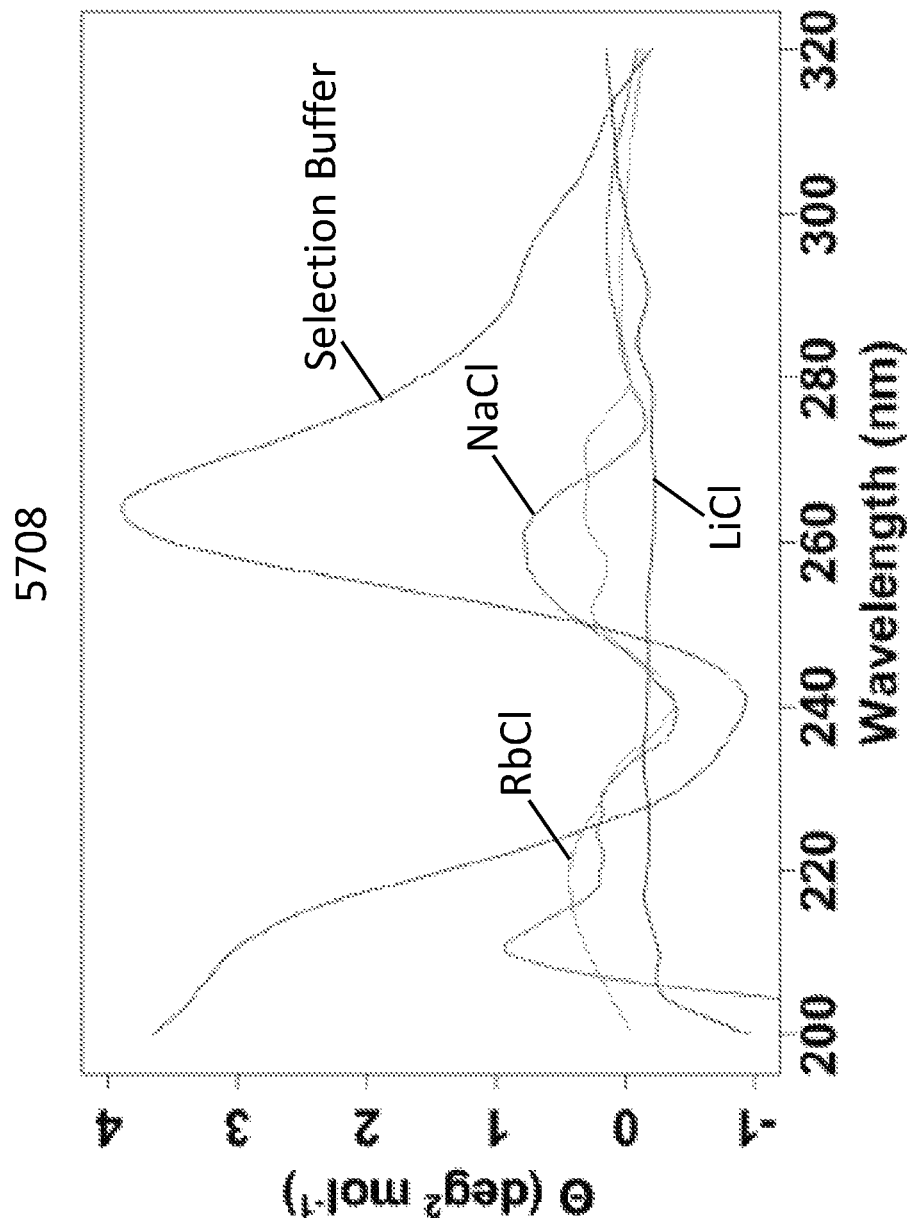

These findings were consistent with the spectra of 3064—the 40 nucleotide parent molecule that forms the same G-quadruplex (Smestad and Maher, supra). Aptamer 5706, however, did not form a similar structure under these conditions. Since in vitro myelin-binding assays and in vivo remyelination studies typically utilize streptavidin-conjugated biotinylated aptamer formulations, the folded structures of 3'-biotinylated 5706 and 5708 were further characterized when conjugated to streptavidin (FIG. 11D). The parallel-stranded G-quadruplex structure of 5708 remained stable when the aptamer was tethered to streptavidin. 5708 also formed a stable G-quadruplex in selection buffer, but 5706 had a significantly less stable secondary structure (FIGS. 12A and 12B, and TABLE 1).

Figure 11E:
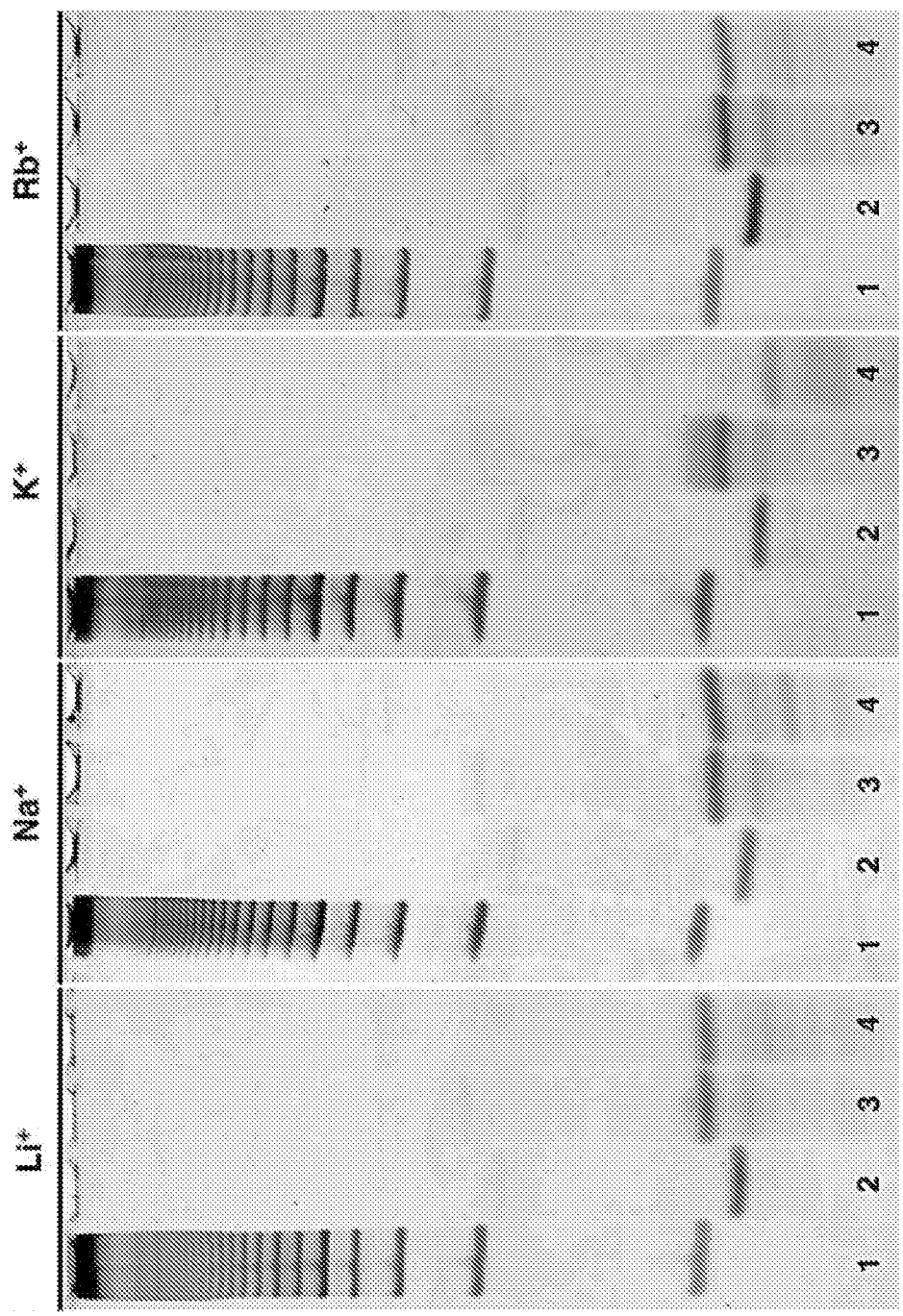
FIG. 11E is an image of a gel after polyacrylamide electrophoretic gel mobility analysis of aptamers under the indicated ionic conditions. Lane 1, duplex DNA reference ladder; lane 2, 5733; lane 3, 5706; lane 4, 5708.

To further confirm the G-quadruplex structure formed by 5708, electrophoretic gel mobility analysis was performed in the presence of various monovalent cations, including Li+, Na+, K+, and Rb+. G-quadruplex structures are preferentially stabilized by K+ ions, resulting in a more compact structure with increased electrophoretic mobility (Bryan and Baumann (2011) *Mol Biotechnol* 49:198-208; Williamson et al. (1989) *Cell* 59:871-880; and Williamson (1994) *Annu Rev Biophys Biomol Struct* 23:703-730). Results are shown in FIG. 11E. Aptamer 5708 (lane 4) was indeed preferentially stabilized by K+ compared to other monovalent cations, consistent with the formation of a G-quadruplex structure. In contrast, the mobility of aptamer 5706 (lane 3) did not change relative to unstructured control dT20 (lane 2), or duplex DNA ladder (lane 1). The relative G-quadruplex stability of each aptamer in various ionic conditions was further confirmed by CD spectroscopy (FIGS. 12A and 12B, and TABLE 1).

Preservation of myelin-binding specificity in different protein conjugates: Biotinylated aptamers were conjugated to streptavidin to form multimers for remyelinating therapy in living mice, as described elsewhere (Nastasijevic et al., supra). These experiments showed that streptavidin conjugation formation was essential for enhanced biodistribution and aptamer-mediated remyelination in mice (Perschbacher et al. (2015) *Nucleic Acid Ther* 25:11-19). Unconjugated aptamer was not effective. The necessity for protein conjugation is not understood, although multimerization may enhance target avidity (Maier et al. (2016) *Mol Ther Nucleic Acids* 5:e321; Chang et al. (2015) *PLoS One* 10:1-16; and Stephanopoulos et al. (2010) *ACS Nano* 4:6014-6020). It also is possible that aptamer conjugation to protein creates a more favorable overall charge density affecting biodistribution and target affinity. Other advantages unrelated to target binding may be conferred by conjugation to streptavidin, such as resistance to nuclease activity by terminal modifications. Larger streptavidin-aptamer complexes could be more resistant to renal clearance than free aptamers, as addressed in some instances by terminal polyethylene glycol modifications to enhance duration of circulation (Tucker et al. (1999) *J Chromatogr B Biomed Sci Appl* 732:203-212).

Figure 13A:
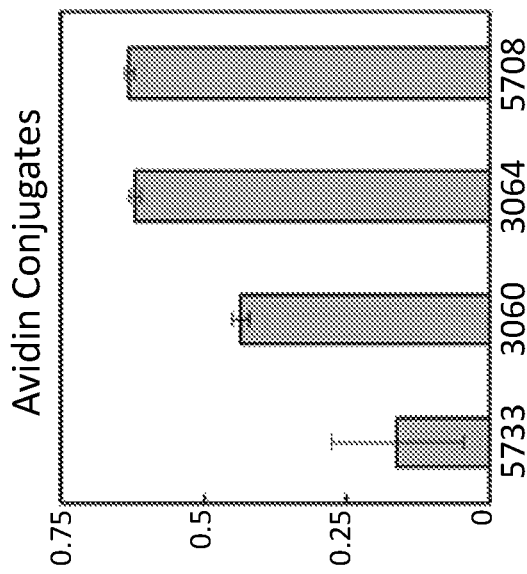
FIGS. 13A-13C are graphs plotting the fraction of biotinylated aptamer bound to myelin after conjugation to streptavidin (FIG. 13A), neutravidin (FIG. 13B), or avidin (FIG. 13C).
Figure 13B:
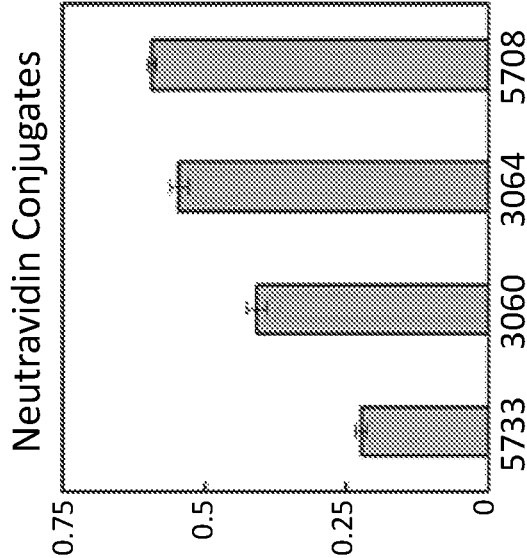
Figure 13C:
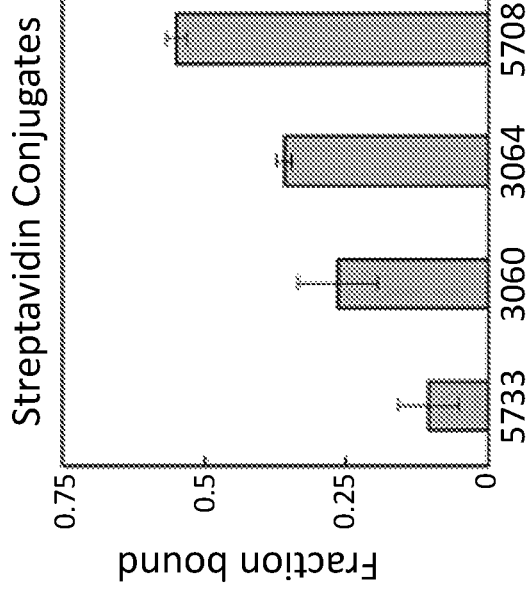

Given the importance of protein conjugation, myelin binding was compared for three common biotin-binding tetramers: streptavidin, neutravidin, and avidin. Streptavidin is a bacterial biotin-binding tetramer with a moderate isoelectric point and low nonspecific binding. Neutravidin is a deglycosylated form of egg white avidin. Streptavidin-aptamer complexes bound myelin when conjugated with 5708, while negative controls 3060 and 5733 bound poorly (FIG. 13A). When neutravidin from egg white was substituted for bacterial streptavidin, myelin binding by negative control molecules was significantly increased. The difference in binding activity between conjugates of 3064 and 5708 remained statistically significant ($p<0.05$; FIG. 13B). Finally, in complexes with avidin (FIG. 13C) binding differences between 3064 and the optimized aptamer 5708 were no longer significant. These results suggested that the identity of the biotin-binding protein used as a conjugation core influences the specificity of the myelin-binding interaction.

Figure 14B:
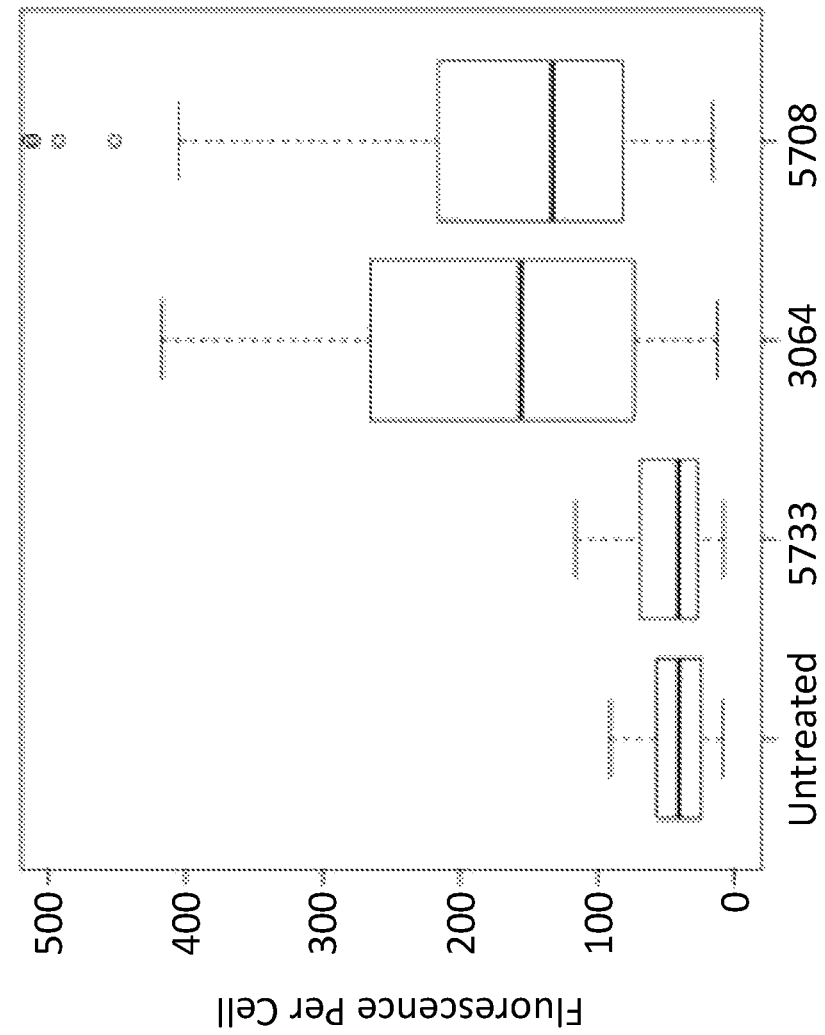
FIG. 14B is a graph plotting quantification of the binding of aptamer-streptavidin complexes.
Figure 14C:
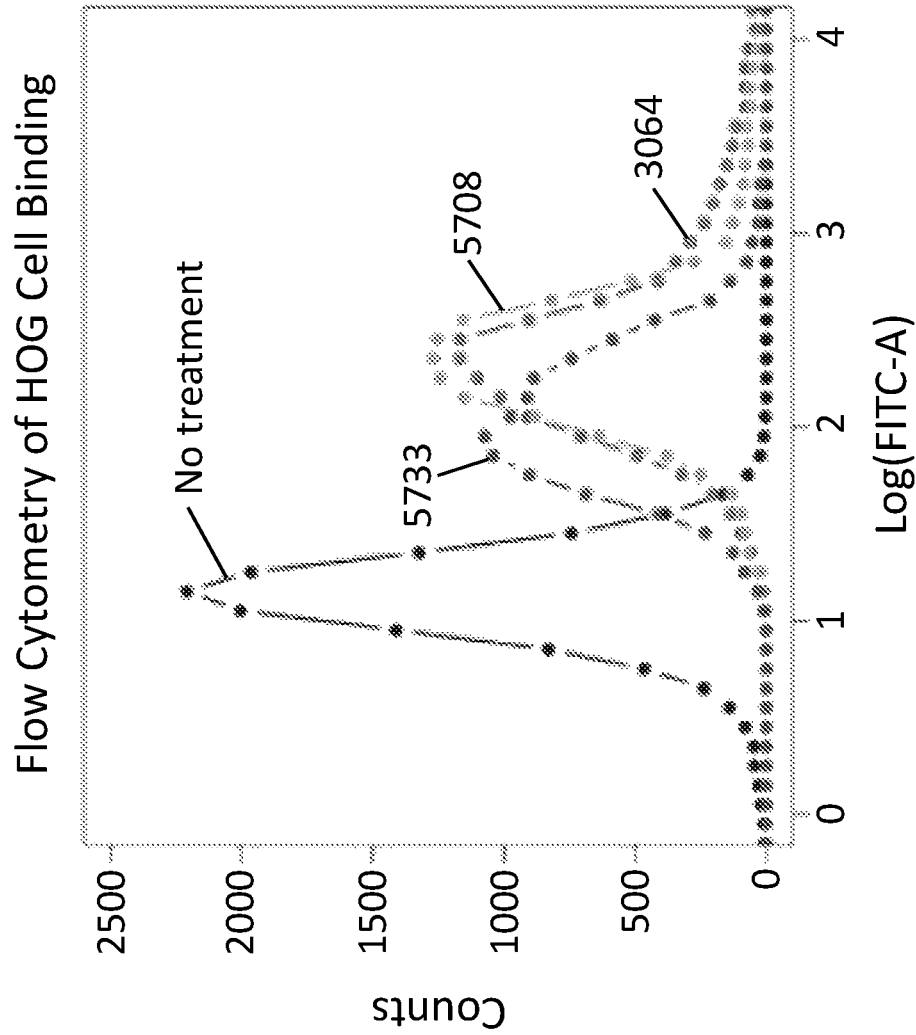
FIG. 14C is a histogram of flow cytometry analysis of binding of aptamer-streptavidin complexes.

Myelin-specific aptamers bind HOG cells: The degree to which streptavidin conjugates of antimyelin DNA aptamers bind the surface of HOG cells was assessed under typical cell culture conditions. The results are shown in FIGS. 14A-14C. Streptavidin complexes of both 3064 and 5708 were capable of strong HOG cell binding relative to controls. Binding was assessed by both confocal microscopy with image quantification (FIGS. 14A and 14B) and flow cytometry (FIG. 14C), with similar results.

TABLE 1

Summary of molar ellipticity values from CD spectroscopy for aptamers 5706 and 5708 in various ionic conditions

| | $\Theta$ (deg$^2$ mol$^{-1}$) 240 nM | $\Theta$ (deg$^2$ mol$^{-1}$) 260 nM |
|---|---|---|
| 5706, 160 mM Li$^+$ | 0.0515 | −0.199 |
| 5706, 160 mM Na$^+$ | −0.723 | 0.114 |
| 5706, 160 mM K$^+$ | 0.0976 | 0.851 |
| 5706, 160 mM Rb$^+$ | −0.935 | 1.338 |
| 5706, Selection Buffer | −0.981 | 1.541 |
| 5706: Strepavidin, 160 mM K$^+$ | −0.369 | 0.481 |
| 5708, 160 mM Li$^+$ | 0.051 | −0.199 |
| 5708, 160 mM Na$^+$ | −0.317 | 0.366 |
| 5708, 160 mM K$^+$ | −0.953 | 3.778 |
| 5708, 160 mM Rb$^+$ | −0.0926 | 0.324 |
| 5708, Selection Buffer | −0.732 | 3.899 |
| 5708: Strepavidin, 160 mM K$^+$ | −0.478 | 2.208 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a pharmaceutically acceptable carrier and a nucleic acid aptamer comprising the sequence set forth in any one of SEQ ID NOS:6 to 19, a fragment of any one of SEQ ID NOS:6 to 19, or a variant sequence having at least 90% identity to the sequences of any one of SEQ ID NOS:5 to 19.

2. The composition of claim 1, wherein the nucleic acid aptamer consists essentially of the sequence set forth in any one of SEQ ID NOS:6 to 19.

3. The composition of claim 1, wherein the nucleic acid aptamer is a multimer.

4. The composition of claim 1, wherein the nucleic acid aptamer is a homodimer, homotrimer, or homotetramer.

5. A method for treating a mammal identified as having a demyelinating disease, wherein the method comprises administering a nucleic acid aptamer to the mammal, and wherein the nucleic acid aptamer comprises the sequence set forth in any one of SEQ ID NOS:6 to 19, a fragment of any one of SEQ ID NOS:6 to 19, or a variant sequence having at least 90% identity to the sequences of any one of SEQ ID NOS:5 to 19.

6. The method of claim 5, wherein the nucleic acid aptamer consists essentially of the sequence set forth in any one of SEQ ID NOS:6 to 19.

7. The method of claim 5, wherein the nucleic acid aptamer is a multimer.

8. The method of claim 5, wherein the nucleic acid aptamer is a homodimer, homotrimer, or homotetramer.

9. The method of claim 5, wherein the demyelinating disease is selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease.

10. A method for promoting neuronal remyelination in a mammal in need thereof, comprising administering to the mammal a pharmaceutical composition comprising a nucleic acid aptamer in an amount effective to promote remyelination, wherein the nucleic acid aptamer comprises the sequence set forth in any one of SEQ ID NOS:6 to 19, a fragment of the sequence set forth in any one of SEQ ID NOS:6 to 19, or a variant sequence having at least 90% identity to the sequence of any one of SEQ ID NOS:5 to 19.

11. The method of claim 10, wherein the nucleic acid aptamer is a multimer.

12. The method of claim 10, wherein the nucleic acid aptamer is a homodimer, homotrimer, or homotetramer.

13. The method of claim 10, wherein the nucleic acid aptamer consists essentially of the sequence set forth in any one of SEQ ID NOS:6 to 19.

14. The method of claim 10, wherein the remyelination is mediated by central nervous system-type myelin producing cells or by peripheral nervous system-type myelin producing cells.

15. The method of claim 10, wherein the mammal is diagnosed with a demyelinating disease.

16. The method of claim 15, wherein the demyelinating disease is selected from the group consisting of multiple sclerosis, idiopathic inflammatory demyelinating diseases, transverse myelitis, Devic's disease progressive multifocal leukoencephalopathy, optic neuritis, leukodystrophies and acute disseminated encephalomyelitis, Guillain-Barré syndrome, chronic inflammatory demyelinating polyneuropathy, anti-MAG peripheral neuropathy, and Charcot-Marie-Tooth disease.

* * * * *